(12) United States Patent
Duensing et al.

(10) Patent No.: US 6,865,494 B2
(45) Date of Patent: Mar. 8, 2005

(54) METHOD AND APPARATUS FOR NOISE TOMOGRAPHY

(75) Inventors: G. Randy Duensing, Gainesville, FL (US); Charles Saylor, Gainesville, FL (US); Feng Huang, Gainesville, FL (US)

(73) Assignee: MRI Devices Corp., Gainesville, FL (US)

( * ) Notice: Subject to any disclaimer, the term of this patent is extended or adjusted under 35 U.S.C. 154(b) by 35 days.

(21) Appl. No.: 10/323,135

(22) Filed: Dec. 18, 2002

(65) Prior Publication Data

US 2003/0160622 A1 Aug. 28, 2003

Related U.S. Application Data

(60) Provisional application No. 60/430,722, filed on Dec. 3, 2001, and provisional application No. 60/341,645, filed on Dec. 18, 2001.

(51) Int. Cl.[7] .............................................. G06F 19/00
(52) U.S. Cl. ........................... 702/38; 702/38; 702/104; 702/179; 702/198; 324/439; 324/633; 324/722; 73/335.05; 600/409; 600/411
(58) Field of Search ............................. 702/38, 49, 65, 702/94, 104, 150–153, 179, 19; 324/633, 439, 207.12; 600/409–411; 73/335.05

(56) References Cited

U.S. PATENT DOCUMENTS

| 4,442,404 A | * | 4/1984 | Bergmann | 324/309 |
| 5,025,222 A | * | 6/1991 | Scott et al. | 324/639 |
| 2002/0103429 A1 | * | 8/2002 | deCharms | 600/410 |

FOREIGN PATENT DOCUMENTS

| WO | WO 91/19454 | 12/1991 |
| WO | WO 00/12005 | 6/2000 |

OTHER PUBLICATIONS

Cooper et al., 'Signal to Noise Improvements in Nuclear Magnetic Resonance Micro–Coils', Jan. 2000, NSF, pp. 1–27.*

Kruger et al., 'Physiological Noise in Oxygenation–Sensitive Magnetic Resonance Imaging', Jun. 2001, ISMRM Paper, pp. 631–637.*

Guru et al., 'Experimental and Theoretical Studies on Electromagnetic Fields Induced Inside Finite Biological Bodies', Jul. 1976, IEEE, pp. 433–440.*

Panin et al.,'An Iterative Approach to Tensor Tomography', Jan. 2001, IEEE, pp. 272–276.*

(List continued on next page.)

Primary Examiner—Marc S. Hoff
Assistant Examiner—Elias Desta
(74) Attorney, Agent, or Firm—Saliwanchik, Lloyd & Saliwanchik

(57) ABSTRACT

The subject invention pertains to an imaging technique and apparatus which can utilize an array of RF probes to measure the non-resonant thermal noise which is produced within a sample, such as a body, and produce a non-resonant thermal noise correlation. The detected noise correlation is a function of the spatial overlap of the electromagnetic fields of the probes and the spatial distribution of the conductivity of the sample. The subject technique, which can be referred to as Noise Tomography (NT), can generate a three-dimensional map of the conductivity of the sample. Since the subject invention utilizes detection of the thermal noise generated within the body, the subject method can be non-invasive and can be implemented without requiring external power, chemicals, or radionuclides to be introduced into the body. The subject imaging method can be used as a stand along technique or can be used in conjunction with other imaging techniques.

19 Claims, 16 Drawing Sheets

OTHER PUBLICATIONS

Brown, B. et al., "Electrical Impedance Tomography,the Construction and Application to Physiological Measurement of Electrical Impedance Images", *Medical Progress Through Technology*, 1987, pp. 69–75, vol. 13, No. 2 Martinus Nijhoff Publishers, Boston, Dordrecht, Netherlands.

Wang, W. et al., "Signal Processing for noise Equalisation Within EIT Images", *IEE Colloquium On Innovations In Instrumentation For Electrical*, 1995, pp. 1–3, The Institution of Electrical Engineers, Savoy Place, London, UK.

Chan, T.F. and Vese, L.A. "Active Contour and Segmentation Models using Geometric PDE's for Medical Imaging" *UCLA CAM Report*, 2001, pp. 00–41.

Cohen–Bacrie, C. and Goussard, Y. "Regularized Reconstruction in Electrical Impedance Tomography Using a Variance Uniformization Constraint" *IEEE Transactions on Medical Imaging*, 1997, pp. 562–571, vol. 16, No. 15.

Kaufman, L. and Neumaier, A. "Regularization of Ill–Posed Problems by Envelope Guided Conjugate Gradients" *J. Comput. Graph. Stat. 6*, 1997, pp. 451–463.

Radai, M.M. et al. "Evaluation of Impedance Technique for Detecting Breast Carcinoma Using a 2–D Numerical Model of the Torso" *Annals of the New York Academy of Sciences*, 1999, pp. 360–369, vol. 873.

Vauhkonen, M. et al. "Tikhonov Regularization and Prior Information in Electrical Impedance Tomography" *IEE Transactions on Medical Imaging*, Apr. 1998, pp. 285–293, vol. 17, No. 2.

Vese, L.A. and Chan, T.F. "A Multiphase Level Set Framework for Image Segmentation Using the Mumford and Shah Model" *UCLA CAM Report*, 2001, pp. 01–25.

\* cited by examiner

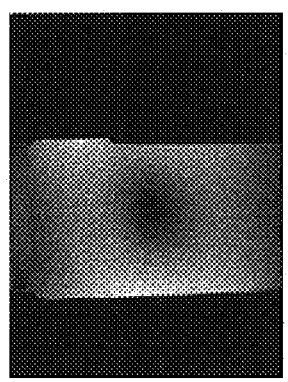 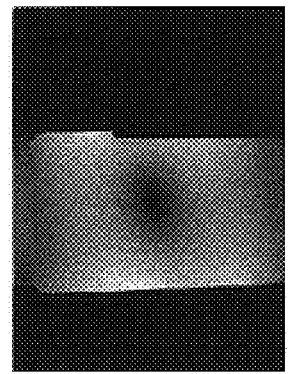
FIG. 2A  FIG. 2B
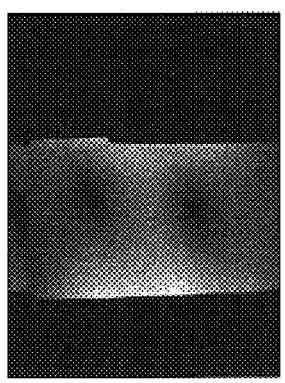 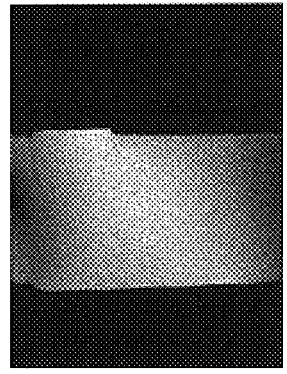
FIG. 2C  FIG. 2D
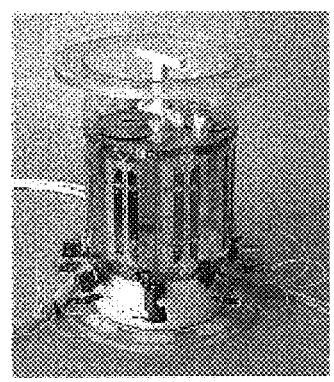 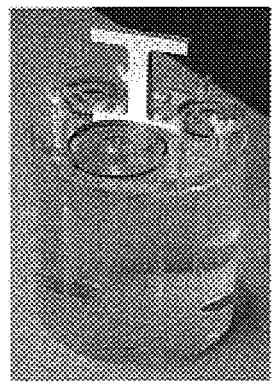
FIG. 4B  FIG. 4C

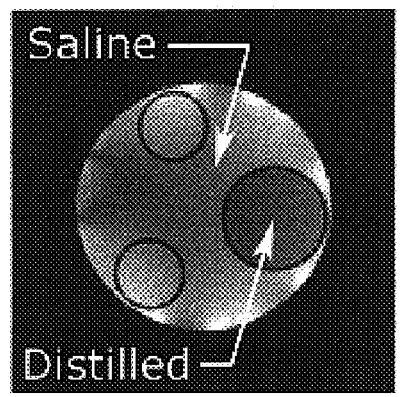
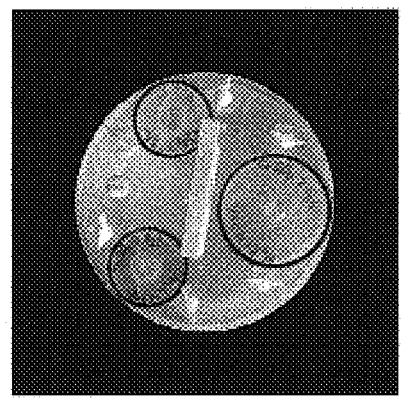
FIG. 5A    FIG. 5B
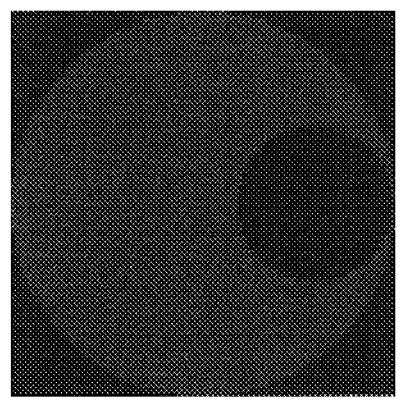
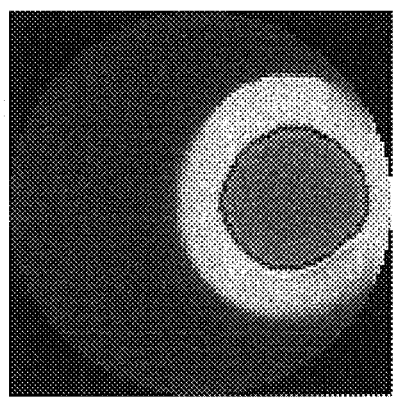
FIG. 7A    FIG. 7B Nearest Neighbor
0 CHANNELS IN-BETWEEN 1 Channel In-between

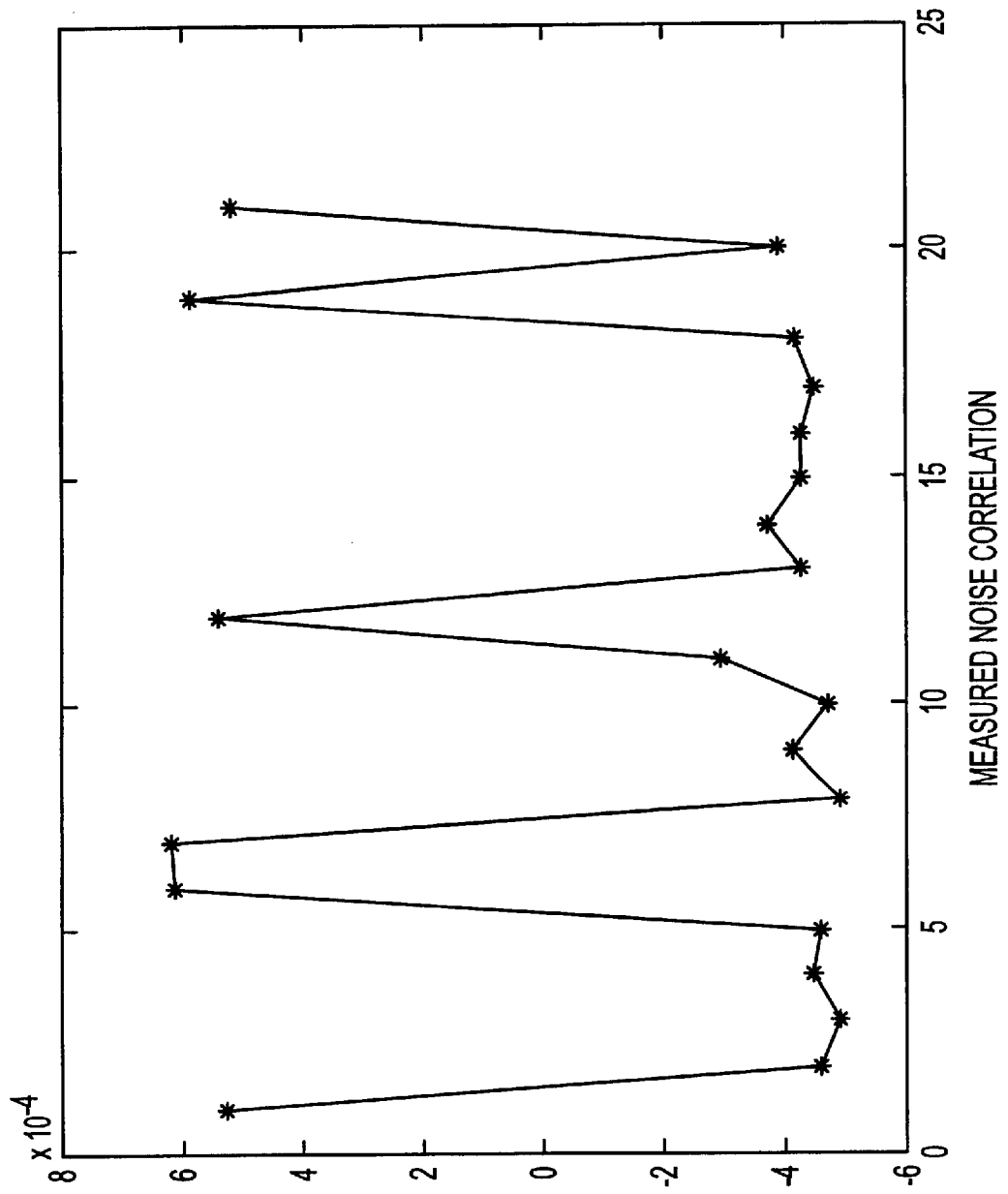

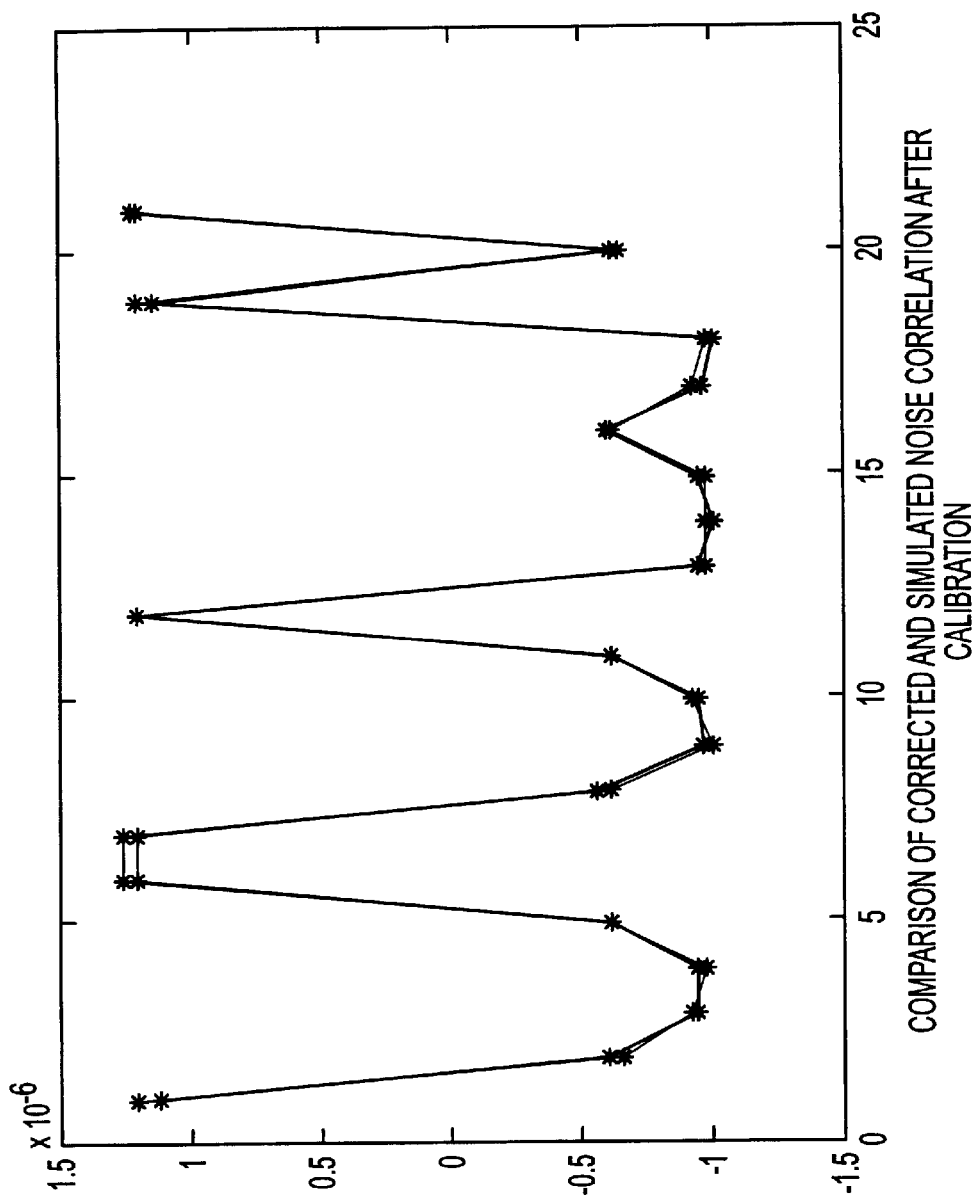

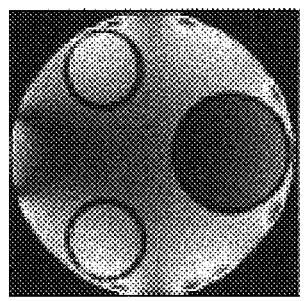
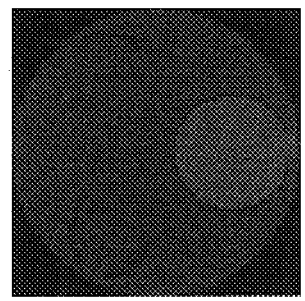
FIG. 12A  FIG. 12B
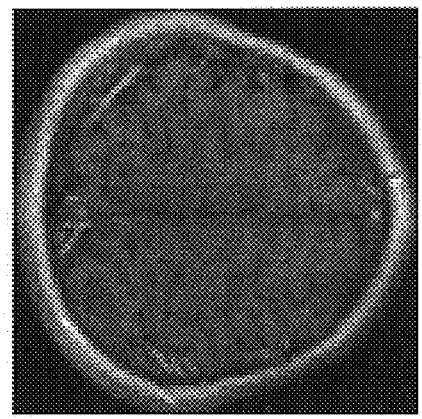
Original MR Image
FIG. 13A
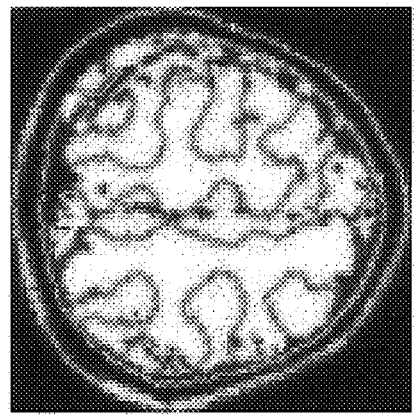
Level set phase 1
FIG. 13B
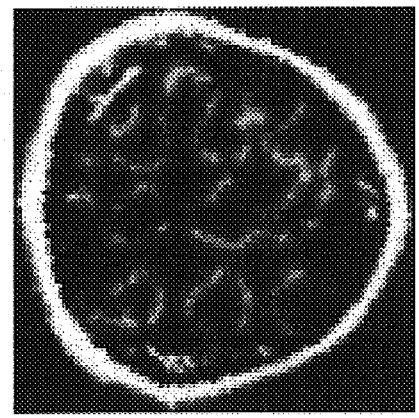
Level set phase 2
FIG. 13C
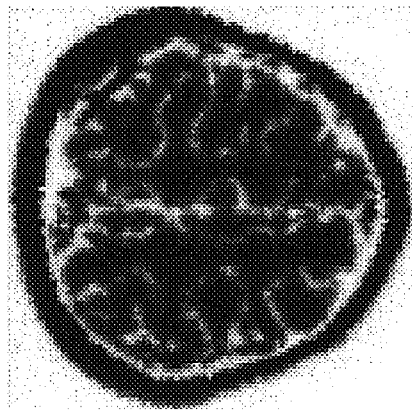
Level set phase 3
FIG. 13D Ideal MR Image Object 1

Object 2

Object 3

Reconstructed
conductivity
distribution map

Ideal MR Image

Object 1

Object 2

Object 3

Reconstructed
conductivity
distribution map

Original MR Image

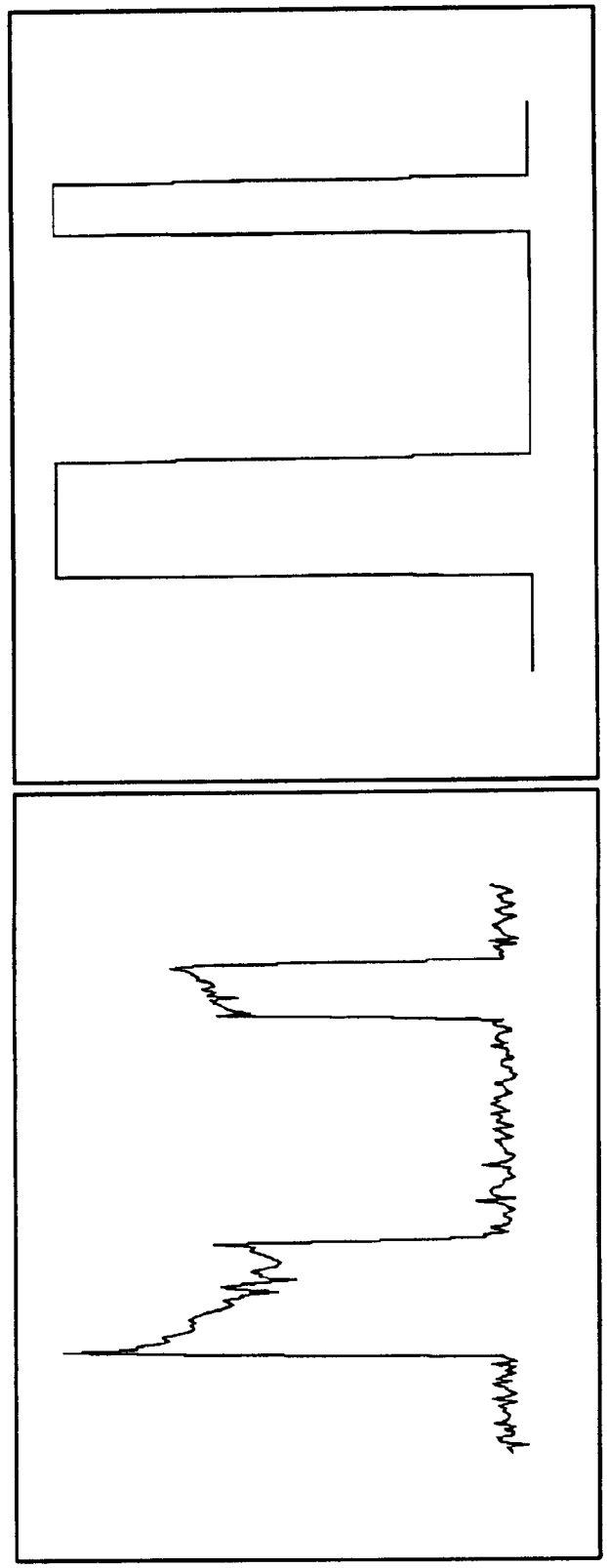

METHOD AND APPARATUS FOR NOISE TOMOGRAPHY

CROSS-REFERENCE TO RELATED APPLICATION

The present application claims the benefit of U.S. Provisional Application Ser. No. 60/341,645; filed Dec. 18, 2001, and of U.S. Provisional Patent Application Ser. No. 60/430,722; filed Dec. 3, 2002, which are hereby incorporated by reference herein in their entirety, including any figure, tables, or drawings.

BACKGROUND OF INVENTION

Historically, the electronic noise, generated within the sample, has not been encoded during the Magnetic Resonance imaging (MRI) process and the pulse sequences and gradient encoding have not encoded the noise. However, the new methods of partially paralleled imaging, for example SENSE and SMASH, demonstrate that the probe sensitivity patterns can be considered encoding functions, and these encoding functions are different from traditional methods. The sensitivity patterns can encode the noise to approximately the same extent that they encode the signal. This is true because the electronic thermal noise of the tissue is normally dominant and the physical size and structure of the coil dictate the acquisition site of the "body" noise. Although the regions of MRI signal acquisition and noise acquisition are similar they are not the same, because the probe's magnetic field is associated with signal acquisition, for example MRI signal acquisition, whereas the probe's electric field is associated with noise acquisition. If several probes and receiver channels are used in MRI signal acquiston, the noise in a given channel can be assumed to be significantly localized by the electric field description of the probe associated with that channel. This indicates that noise can have some information content associated with it, since the noise originates in tissues of the body and is acquired in a predictable way via a local probe. Noise can have an associated spatial encoding capability. This association can exist when the noise originates in tissues of the body and is acquired in a predictable and repeatable way by means of a local probe. The subject Magnetic Resonance Noise Tomography (MR-NT) technique can extend this to measuring the covariances of noise within a multiple receiver system. This is important because, in principle, the amount of non-sample noise is largely irrelevant since correlating the two noise outputs greatly reduces or eliminates the uncorrelated noise via averaging.

BRIEF SUMMARY

The subject invention pertains to an imaging technique and apparatus which can utilize an array of RF probes to measure the non-resonant thermal noise which is produced within a sample, such as a body, and produce a non-resonant thermal noise correlation. The detected noise correlation is a function of the spatial overlap of the electromagnetic fields of the probes and the spatial distribution of the conductivity of the sample. The subject technique, which can be referred to as Noise Tomography (NT), can generate a three-dimensional map of the conductivity of the sample. Since the subject invention utilizes detection of the thermal noise generated within the body, the subject method can be non-invasive and can be implemented without requiring external power, chemicals, or radionuclides to be introduced into the body. The subject imaging method can be used as a stand along technique or can be used in conjunction with other imaging techniques.

BRIEF DESCRIPTION OF DRAWINGS

FIG. 2A shows the approximate functional form of the π coil in the FACT array, $B_0$ field perpendicular to the axis of the array, the MRI signal is proportional to the y component of the B1 field of the coil. In this coil the signal is max at the ends and min in the center.

FIG. 2B shows the approximate functional form of the π coil in the FACT array, $B_0$ field perpendicular to the axis of the array, the MRI signal is proportional to the y component of the B1 field of the coil. In this coil the signal is max at the ends and min in the center.

FIG. 2C shows the approximate functional form of the π coil in the FACT array, $B_0$ field perpendicular to the axis of the array, the MRI signal is proportional to the y component of the B1 field of the coil. In this coil the signal is max at the center then a min and getting larger to the outside.

FIG. 2D shows the approximate functional form of a linear coil in the FACT array, $B_0$ field perpendicular to the axis of the array, the MRI signal is proportional to the y component of the B1 field of the coil. In this coil the signal is max the center and fairly flat over the length.

FIG. 4B is the coil used in a two-dimensional experiment.

FIG. 4C shows a phantom imaged via the subject method.

FIG. 5A shows the MRI image of the 197 mm diameter phantom using the 8 channel array. In the MR Image, the 3" ID acrylic tube is filled with Distilled water. The rest of the phantom is filled with a saline solution of 2 g/L $Cu_2SO_4$ and 4.5 g/L NaCl.

FIG. 5B shows a photograph of the 197 mm diameter NT Phantom

FIG. 7A shows digitized image of phantom FIG. 7B shows a reconstructed image of the phantom shown in FIG. 7A

FIG. 9B shows the measured noise correlation

FIG. 9C shows a comparison of corrected and simulated noise correlation after calibration.

FIG. 12A shows the referenced MR image

FIG. 12B shows the solved relative conductivity of saline solution, water and plastic is 1.0000, 0.1873 and 0.1230.

FIGS. 13A–13D show images relating to an example of segmentation of MRI by using the multiphase approach in accordance with the subject invention.

FIGS. 16A–16C display the segmentation result of a one dimensional experiment in accordance with subject invention.

DETAILED DISCLOSURE

Figure 1B:
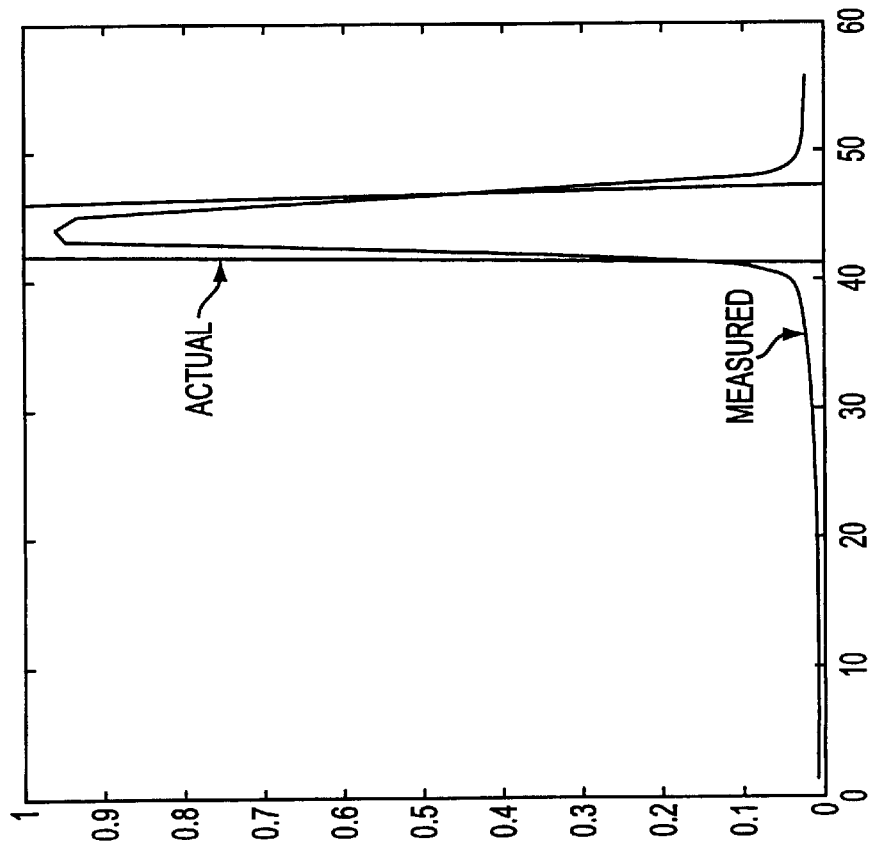
FIG. 1B shows the result of an experiment using MMSLS in accordance with the subject application.

The subject Noise Tomography technique can use the non-resonant electronic thermal noise of the tissue sample, detected by an array of RF probes and the known/calculated overlap of the electromagnetic fields of the probes, to determine the distribution of the conductivity in the sample. Electronic thermal noise is a basic property of all matter and has been well characterized in both the 1-D (Johnson/Nyqusit) and 3-D (Black Body Radiation) cases. The subject NT technique can be based on a combination of the fluctuation dissipation theorem and the principle of reciprocity. The noise correlation between the different channels in an array of RF probes can be used to plot the conductivity distribution within the sample.

When an oscillating RF probe is placed near a conducting sample, the sample dissipates energy from the coil and changes the impedance of the coil. This change in impedance is a function of the internal impedance of the probe and of the coupling between the sample and the probe. From Thevenin's theorem, the thermal noise power detected across a circuit is proportional to the equivalent resistance of the circuit and, therefore, if an RF probe is moved with respect to the sample and the resulting change in noise power is measured, the change in coupling between the sample and the coil can be determined. Keeping the probe in a fixed location and changing the conductivity of the sample can also change the coupling between the sample and the coil and can have a similar effect on the impedance of the circuit and the detected noise power.

A one-dimensional map of the sample conductivity can be constructed by moving the probe at a fixed distance from the surface of the sample and measuring the changes in the sample noise. Adding an array of coils, which can be measured in parallel, can increase the sampling rate, and therefore the imaging rate. As each coil position can provide one piece of information, in order to determine N independent parameters about the sample, a minimum of N independent coil positions can be measured.

In order to increase the amount of information about the sample obtained from any given probe position, and to reduce the effects of non-sample noise sources, the noise correlation between different coils in an array of coils can be measured. Using the normalized noise covariance can provide up to N(N-1)/2 different pieces of information about the sample from each position of the coil array, as well as reducing the effects of non-sample related detector noise sources. The noise correlation between channels is equal to the $\int \vec{E}_j(\vec{r}) \cdot \sigma(\vec{r}) \cdot \vec{E}_k(\vec{r}) dV$ where E1, $E_k$ are the electric field resulting from the two probes at the point r in space and $\sigma(r)$ is the conductivity at the point r in space.

The subject imaging technique can produce a conductivity map of an object based on the noise correlation detected within an array of RF probes. The subject method can be applied over a 1 MHz to 100 GHz range of RF frequencies. The limit on the low frequency side is in the 1 to 10 MHz range because thermal noise of the sample should be greater than thermal noise of the probe. The sample should be the primary component of the energy dissipation in the system. The high-end of the frequency range, for medical imaging can be defined by the penetration depth. The sensitivity of the probes to EM fields generated within the body can be determined by the magnitude of the Electric field generated by the probe when the probe is driven by a unitary source. If the penetration depth is too short the electric field profile within the sample will be large near the surface decreasing rapidly into the body. As a result the probes will only be sensitive to EM fields generated at near the surface. The result of this is that maximum reasonable operating frequency for this technique, for medical imaging, is somewhere between 10 and 100 GHz.

FIG. 1 shows a specific embodiment of a coil array which can be utilized in accordance with the subject invention. Other coil arrays can be utilized as well. This coil array uses Fourier Array Coil Technology (FACT). A spiral birdcage can produce a magnetic field that is sinusoidal in the X and Y directions. Since the sines and cosines form an orthogonal basis, multiple coils with different spatial frequencies can also be substantially orthogonal. The four coil array shown in FIG. 1 incorporates a $+\pi$ rotation, a $-\pi$ rotation, a 0 rotation, and a $2\pi$ rotation. With supplemental isolation methods, adequate isolation can be achieved between all pairs of elements.

The subject invention also relates to a method of determining the temperature of a sample as a function of position, comprising:

measuring electromagnetic fields from a sample via a plurality of probes, wherein the plurality of probes detect time-varying electromagnetic fields;

determining the measured correlation. $M_{ij}(\Omega)$, between at least one pair of probes;

determining the temperature of the sample as a function of position, based on the following relationship:

$$M_{ij}(\Omega) = \int_\Omega \vec{E}_i(\sigma,x) \cdot T(x) \cdot \vec{E}_j(\sigma,x) dx$$

where T(x) is the temperature of the sample as a function of position and $E_j(\sigma, x)$ is the electric field created in the sample at position x by probe j when driven by a unit source.

EXAMPLE 1

A one-dimensional experiment was preformed using a four-coil FACT array, with a length of 55 cm long and diameter of 18 cm. The electromagnetic fields in the sample region for each of the four elements and the z dependence of the six independent values in the covariance matrix with respect to the insertion of a cylindrically symmetric phantom into the coils. The z dependence of normalized noise covariance matrix in this calculation is assumed to be proportional to $\int \vec{E}_k \cdot \sigma \cdot \vec{E}_m^* r dr d\theta$. This assumption comes from the reciprocity theorem which relates the voltage detected on each channel, for an arbitrary current, J, at some location within the sample, will be proportional to $J \cdot E_k$, where $E_k$, is the electric field generated by a unitary amplitude oscillating current on the $k^{th}$ probe. Using the assumption that the local current distribution within the sample can be described by a Thevenin's current source equivalent circuit for the Nyquist/Johnson model of the electronic thermal noise, J obeys Gaussian distribution with mean $\vec{J} = 0$ and a variance $J^2 \approx 4kT\Delta f\sigma$. From this we can calculate the dependence of the covariance $CV_{km} = (J \cdot E_k^*)(J \cdot E_m^*)$. The only components of the covariance for which the time average is not equal to zero are $J^2(E_k^* \cdot E_m^*)$ or $CV_{km} \approx \sigma(E_k^* \cdot E_m^*)$. (Wilbur B Davenport, Jr. William L Root (1987) "An Introduction to the Theory of Random Signals and Noise" The Institute of Electrical and Electronics Engineers Inc.)) The total thermal noise on each channel can be approximated using a combination of the probe resistance and the effective resistance of the sample, which results from probe sample coupling, $\int \vec{E} \cdot \sigma \cdot \vec{E}_k^* dV$.

Under the assumption that each channel's impedance is independent of the sample location. The combination of channel-channel coupling and the probe matching conditions make it so that the measured covariance can be described by the function: $CO_{km} = A_{km} \int \vec{E}_k \cdot \rho(z) \cdot \vec{E}_m dV + B_{km}$. In order to determine these constants a calibration was preformed using 14.6 cm diameter by 9.7 cm long MRI phantom. FIGS. 2A–2F show a plot of the 9 point calibration and the predicted behavior of the six covariances. The covariances in this experiment were measured using a GE 1.5 T MRI and actual position of the phantom was determined from an MRI image. Computer simulations and experiments have shown the subject technique works for one-dimension with a simple constant impedance sample.

The subject NT technique can measure the correlation in the detected noise between different probes within an array of RF probes. In a specific embodiment, the noise signals detected on each channel between each pair of channels can be digitally mixed by, for example, amplifying and filtering the signal from each channel, converting the signal to digital using an A/D converter, and then digitally filtering, processing, multiplying and filtering the signal from each pair of channels. A high speed Analog to Digital converter which can directly convert the signal to digital over our entire frequency band can be used. The digital design can permit changes in detection frequency, bandwidth, and filters in order to minimize the effects of external noise sources and increase the system sensitivity.

The subject technique of NT is related to Electrical Impedance Tomography (EIT) in the sense that both techniques generate an impedance map of the measured sample conductivities. EIT functions by generating an electrical current distribution in the body, either through direct contact or inductive coupling, and then measuring this distribution through an array of detectors designed to measure either the current or the voltage (using direct contact probes), or the induced electric or magnetic fields (using an array of capacitance, induction or magnetic field probes (SQUID)). These measurements are then used to calculate an impedance map of the measured sample (EIT). At present Electrical Impedance Tomography is the focus of significant research attention. The Journal of Measurement, Science and Technology dedicated the August, 2001 issue solely to EIT topics.

EIT uses computer algorithms to generate an image from the measured current distribution. Similar computer algorithms can be used to generate an image from the measured correlations for the subject NT image reconstruction. The important difference between NT and EIT imaging techniques is that NT uses the noise sources associated with the internal structure of the tissue instead of externally introduced electrical or magnetic currents.

The subject NT method is similar to that of EIT imaging except that the sources used are the noise sources associated with the internal structure of the tissue. It is a basic principle of physics that materials which are resistive (i.e. dissipate electric power) also generate noise and we are using this duality principle to obtain the same impedance information used in EIT.

The subject method can involve measuring the non-resonant thermal noise correlation that is produced within a body. The subject invention can utilize an array of RF probes to detect such noise correlation. The detected noise correlation can be a function of both the spatial overlap of the electromagnetic fields of the probes and the spatial distribution of the conductivity of the sample. The subject method can also involve additional methods of imaging, such as MR imaging, and the cooperation of additional imaging, such as MRI imaging and measuring non-resonant thermal noise correlation. The inversion to regions of constant conductivity can be guided by MR image data, greatly improving the accuracy, speed, and stability of the inverse problem. The use of MR to provide regionalization data converts from an under-determined to an over-determined inversion problem and can be elegantly performed simultaneously with no extra experiments beyond the MR imaging to be done, and, optionally, a short noise only scan.

A specific embodiment of the subject invention can be referred to as MR Noise Tomography (MR-NT). MR-NT can generate a three-dimensional map of the conductivity of the sample and can result in a set of slices (or 3D volume) in which the contrast of the image can be related to the conductivity. In a specific embodiment, the subject invention can be based on detection of the thermal noise generated within the body, such that the subject MR-NT method can be a non-invasive technique which introduces no additional power, chemicals, or radio-nuclides into the body. In a specific embodiment, a modified MR imaging technique in accordance with the subject invention can be designed to produce a conductivity map of the human breast based on the noise correlation detected within an array, with the appearance of a segmented MR image. High resolution, high sensitivity conductivity maps within a reasonable time can be achieved with the MR-NT technique in three dimensions.

Historically, the electronic thermal noise generated within a sample has not been encoded during the Magnetic Resonance Imaging (MRI) process. The pulse sequences and gradient encoding do not encode the noise, but the new methods of partially parallel imaging (SENSE, SMASH, etc., [PWSB] [SM1] [SM2] [WSE] [WSM]) demonstrate that the probe sensitivity patterns are encoding functions for the MRI signal. The sensitivity patterns also encode the noise to approximately the same extent as they encode the signal. This is true because the electronic thermal noise of the tissue is normally dominant and the physical size and structure of the coil dictate the acquisition site of the 'body' noise. Although the regions of MRI signal acquisition and noise acquisition are similar they are not the same, because the probe's magnetic field is associated with MRI signal acquisition whereas the probe's electric field is associated with noise acquisition. If several probes and receiver channels are used in MRI signal acquisition, the noise in a given channel can be assumed to be significantly localized by the electric field profile of the probe associated with that channel. This indicates that noise can have an associated spatial encoding capability. The association exists because the noise originates in tissues of the body and is acquired in a predictable and repeatable way by means of a local probe. A specific embodiment of the subject NT technique refines existing technology by utilizing the covariances of noise received within a multiple receiver system. This is important because, in principle, the amount of non-sample noise can be largely irrelevant since correlating the two noise outputs can eliminate the uncorrelated noise by averaging. To determine the distribution of the conductivity in the sample, the subject MR-NT technique can use the non-resonant electronic thermal noise of the tissue sample, detected by an array of RF probes, and the known, or calculated overlap of the electromagnet fields of those probes. Electronic thermal noise is a basic property of all matter and has been well characterized in both one-dimensional (Johnson/Nyquist) and three-dimensional (Black Body Radiation) cases. The subject MR-NT technique can combine the fluctuation dissipation theorem, the principle of reciprocity, and MR imaging. The subject MR-NT technique can use the noise correlation between the different channels in an array of RF probes to plot the conductivity distribution within the sample. It may be desirable to rotate or translate the probe with respect to the tissue to obtain more tomographic perspectives.

When a RF probe is excited near a conducting sample, energy in the probe is dissipated in the sample and the impedance of the probe is changed. This change in impedance is a function of the internal impedance of the probe, the coupling between the sample and the probe, and the electrical properties of the sample. Thevenin's theorem shows that the thermal noise power detected across a circuit is proportional to the equivalent resistance of the circuit. Therefore, if an RF probe is moved with respect to the sample and the resulting change in noise power is measured, the change in coupling between the sample and the coil may be determined. A similar effect on the impedance of the circuit and the detected noise power will occur if the probe is kept in a fixed location and the conductivity of the sample changed.

Utilizing these principals, a one-dimensional conductivity map of the sample may be constructed by simply moving the probe at a fixed distance from the surface of the sample and measuring the changes in the sample noise. Adding an array of coils, which are measured in parallel, can increase the sampling rate and, therefore, the imaging rate. This arrangement, however, will determine only one piece of information per coil position. In order to determine n independent parameters about the sample, a minimum of n independent coil positions can be measured.

In order to increase the sample information obtained from any given probe position and to reduce the effects of non-sample noise sources, the noise correlation between different coils in an array of coils can be measured. Using the normalized noise covariance can provide up to n(n-1)/2 different pieces of sample information from each position of the coil array and will reduce the effects of non-sample related detector noise sources. In a specific embodiment, the subject method it is assumed that the noise correlation between channels is proportional to:

$$\int \vec{E}_j(\vec{r}) \cdot \sigma(\vec{r}) \cdot \vec{E}_k(\vec{r}) dV$$

where $E_j$, $E_k$ are the electric field resulting from the two probes at the point r in space and $\sigma(r)$ is the conductivity at the point r in space.

The modern field of medical imaging is composed of a significant number of techniques, each of which produces a two- or three-dimensional map of a different characteristic of the tissue sample within the body. These characteristics include, for example, electromagnetic scattering cross section (X-ray, CT), radionuclide concentrations (PET), scattering cross section of acoustic waves (ultrasound), nuclear and electron magnetic spin density (MRI), electrical sources (EEG, EKG, ESI), and electrical conductivity (EIT, MIT).

Each of the characteristics measured can be used, in different ways, for diagnostic imaging.

The subject MR-NT technique can be designed to use the correlations in the detected electronic thermal noise in an RF probe array and the relationship between conductivity and the noise power coupled between the sample and probe to measure the electrical conductivity distribution within the sample. Some of the ways that electrical conductivity is used in diagnostic imaging have been documented and include: Gastrointestinal and Esophageal Function [BMLBBJR] [WSBCB], Hyper- or Hypothermic treatment of malignant tumors [Duck F. A.] [MTBHLWP], imaging of the Head [CHBB] [MBA] [H.D.S], Pulmonary Function [HSBB], Cancer detection [BB2] [C.N] [MSM], measurements of cardiac output [J.C.B] and investigation to locate the focus of epileptic seizures [WZP]. In addition Transscan Medical (Israel) has developed and implemented a system for use as an adjunct to mammography. This is basically an EIT method for breast cancer early stage screening.

The subject MR-NT technique is significantly different from the other strategies used in medical imaging. In a specific embodiment, the subject MR-NT technique can provide similar information as Electrical Impedance Tomography (EIT) [BB1], such as an impedance map of the measured sample conductivities, constrained by a prior MR imaging set. EIT functions by generating an electrical current distribution in the body through inductive or capacitive coupling, or by direct contact. EIT then measures this distribution through an array of detectors, designed to measure either the current or the voltage (using direct contact probes), or the induced electric or magnetic fields (using an array of capacitance, induction or magnetic field probes (SQUID)). These measurements are then used to calculate an impedance map of the measured sample (EIT). At present, EIT is the focus of significant research attention. The Journal of Measurement, Science and Technology dedicated the August, 2001 issue solely to EIT topics.

EIT uses computer algorithms ([BB1][KY][KN1][KN2] [VVKSK] [VO] [BG] etc) to generate an image from the measured current distribution. The subject MR-NT method can use similar computer algorithms to generate an image from the measured noise correlations for MR-NT image reconstruction. The conductivity measurement of the MR-NT technique is similar to that of EIT imaging. The sources used with respect to the subject MR-NT technique are the noise sources associated with the internal structure of the tissue instead of externally introduced electric or magnetic fields as used in EIT imaging. It is a basic principle of physics that materials which are resistive (i.e. dissipate electric power) also generate noise. This duality principle is being used to obtain the same, or similar, impedance information used in EIT.

Some new techniques named MR-EIT [KWYK] [OEI1] [OEI2] were introduced recently. MR-EIT integrates EIT and MRI using previously acquired MR images to guide the EIT. The subject MR-NT method can produce impedance maps similar to those obtained using MR-EIT imaging.

The subject invention can be an extension of MRI, the most widely used diagnostic imaging modality. Specific embodiments of the subject technique can be almost entirely non-invasive and potentially highly informative. The subject invention can utilize the information content of random noise in heterogeneous materials.

EXAMPLE 2

One-Dimensional Embodiment of the Subject MR-NT Technique

In a one dimensional embodiment of the subject MR-NT method and apparatus, a coil array was utilized. The coil array uses Fourier Array Coil Technology (FACT) [DGR], pioneered by MRI Devices Corporation. of the coil array can also incorporate one or more versions of a spiral birdcage introduced by Alsop, et al [ACM]. A spiral birdcage coil can produce a magnetic field that is nearly sinusoidal in the X and Y directions. Because the sines and cosines form an orthogonal basis, and if the endring currents are ignored, noise sensitivity functions for multiple FACT coils with different spatial frequencies should form a nearly orthogonal set for a uniform sample.

A FACT coil array consisting of four coils including a $-\pi$ rotation, a 0 rotation, a $+\pi$ rotation and a $2\pi$ rotation, as shown in FIG. 3-1, was used in the one-dimensional experiment of the MR-NT technique.

With supplemental isolation methods, adequate isolation from inductive coupling was achieved between all pairs of elements. A short version of this coil array (approximately 24 cm long and 20 cm in diameter) was used to make MR images of a uniform MRI phantom when the coil was oriented perpendicular to the static B field. The MR images are shown in FIGS. 2A–2D and show the approximate functional form of the magnetic field in the FACT array.

A one-dimensional experiment was performed using a four-coil FACT array, with a length of 55 cm and diameter of 18 cm. The electromagnetic fields in the sample region for each of the four elements of the FACT array were calculated using Biot-Savart pseudo-static methods. Using these field values the z-dependence of the six independent values in the covariance matrix, with respect to the insertion of a cylindrically symmetric phantom into the coil array was calculated. The z-dependence of the normalized noise covariance matrix in this calculation is assumed to be proportional to $\int \vec{E}_k \cdot \sigma \cdot \vec{E}_m^* r dr d\theta$.

This assumption comes from the reciprocity theorem: the voltage detected on each channel, for an arbitrary current J, at some location within the sample will be proportional to $J \cdot E_k$, where $E_k$ is the electric field generated by a unitary amplitude oscillating current on the $k^{th}$ probe. Assuming that the local current distribution within the sample can be described using a Thevenin's equivalent current source, the equivalent circuit for the Nyquist/Johnson model of the electronic thermal noise, will consist of a current source were J obeys Gaussian distribution with mean $\vec{J} = 0$ and a variance $J^2 = 4kT\Delta f \sigma$. The dependence of the covariance becomes $CV_{km} = (J \cdot E_k^*)(J \cdot E_m^*)$. The only components of the covariance for which the time average is not equal to zero are $J^2(E_k^* \cdot E_m^*)$ or $CV_{km} \approx (E_k^* \cdot \sigma \cdot E_m^*)$. [DR] The total thermal noise on each channel can be approximated using a combination of the probe resistance and the effective resistance of the sample, which results from probe sample coupling, $\int \vec{E}_k \cdot \sigma \cdot \vec{E}_k^* dV$.

FIGS. 3A–3F display the z-dependence of $\int \vec{E}_k \cdot \vec{E}_m^* dV$ assuming a load 14.6 cm in diameter. Given the combination of channel-channel coupling and the probe matching conditions, the measured covariance can be described by the function: $CO_{km} = A_{km} \int \vec{E}_k \cdot \rho(z) \cdot \vec{E}_m dV + B_{km}$. The additional parameters represent the amount of noise associated with sources other than the sample ($B_{km}$) and differences in effective gain between channels ($A_{km}$). In order to determine the constants $A_{km}$ and $B_{km}$, a calibration was performed using a 14.6 cm diameter by 9.7 cm long MRI phantom. FIGS. 3A–3F demonstrate the ability to accurately simulate noise correlation behavior given the calibration of the six covariances. The covariances in this experiment were measured using a GE 1.5 T MRI and the actual location of the phantom was determined from an MRI image.

In each figure, the simulated covariance when the phantoms center was located at each of the 9 points on the graph is indicated and the corresponding measured covariances using the MRI system, with the phantom at each position, is also indicated. The strong correspondence between the simulated and measured curves indicate that the noise covariance data can be used to approximately predict the one dimensional location of the phantom in the coil from the noise data only.

Figure 10:
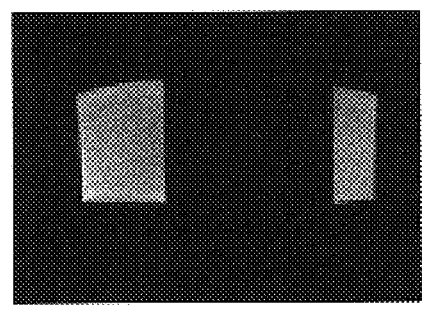
FIG. 10 shows original image identical to image in FIG. 16A
Figure 11:
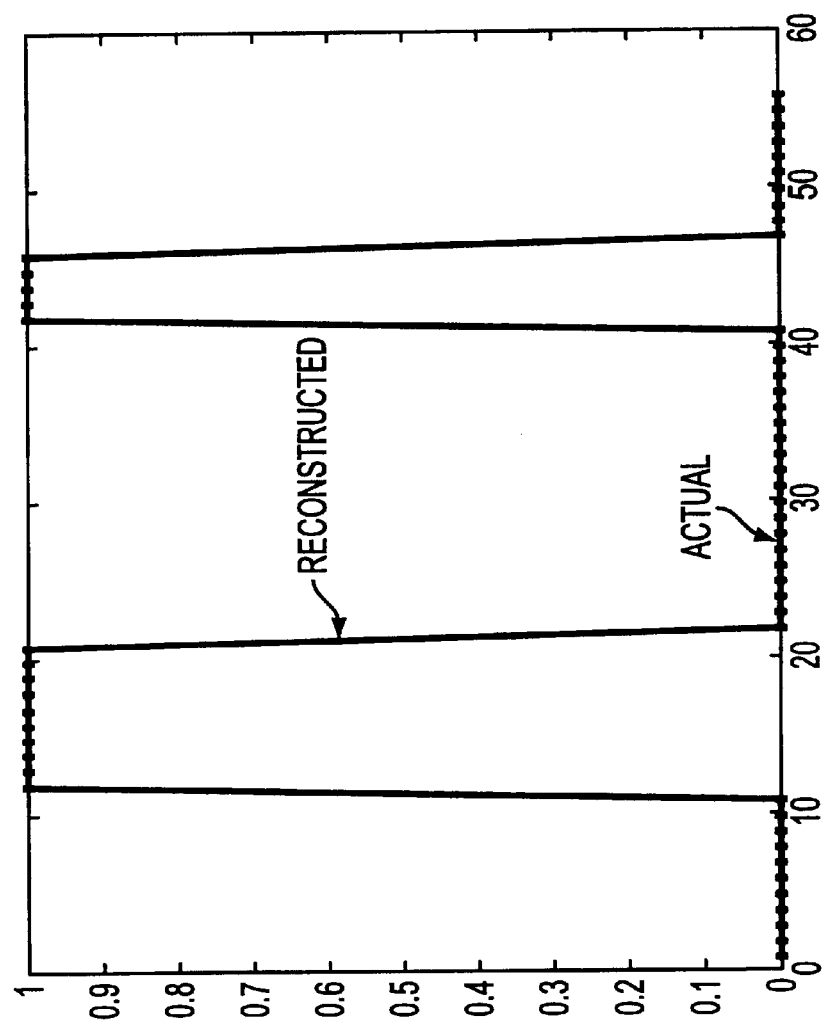
FIG. 11 shows the results of a one-dimensional experiment, indicating the reconstructed conductivity (curve) and actual distribution (dots).

FIG. 10 displays the MR image in a one-dimensional test. The phantom consists of two discs with a diameter of 16 cm and width 10-cm and 5-cm. FIG. 11 displays the reconstructed one-dimensional conductivity distribution (the solid curve) based on the given MRI image. The dots on FIG. 11 display the actual conductivity distribution.

Accordingly, the subject method correctly produced the relative conductivities in 5 regions, given 6 covariances.

EXAMPLE 3

Two Dimensional Experiment of the Subject MR-NT Method and Apparatus

A specific phantom and coil array were produced to be used in conjunction with a 1.5 T 8 channel MRI system. A two-dimensional test of the subject MR-NT method was preformed using an RF array, as shown in FIG. 4B, that was based on an eight-channel MRI head coil by MRI Devices Corporation. The array incorporates eight resonance tuned loop probes, each loop sweeping an angle of 57 degrees, with a height of 180 mm. The coil array was constructed on a 215.9 mm(8.5") OD Acrylic tube. Each of the coils was overlapped with its nearest neighbors, providing approximately 20 dB of isolation from its nearest neighbors. This coil is a poor design for MR-NT for the same reason that it is a good design for an MRI coil: because of the symmetrical design, the electric field at the center of the coil is zero. The coil does have significant electric fields in the perimeter, and the phantom was designed with this in mind.

In order to study the noise correlation effects in two dimensions, a phantom was constructed which is effectively two-dimensional. The design of the phantom is shown in FIGS. 4B, 5A, and 5B. The phantom is constructed of a 197 mm (7.75") ID by 180 mm long acrylic tube that is filled with a solution of $Cu_2SO_4$ (2.0 grams/Liter) and NaCl (4.5 grams/Liter). The conductivity of this solution is on the order of 0.8 S/m. There are three smaller acrylic tubes, each of which is 180 mm long, contained within the 197 mm OD tube. These can be filled with either distilled water or saline solutions of different concentrations in order to adjust the conductivity. This phantom has been designed for translational symmetry over its full length, producing an effective two-dimensional system. The phantom was designed to rotate about its axis in five degree steps, in order to increase spatial resolution.

The subject MR-NT method can involve determining a noise correlation basis. For the two-dimensional case, the contribution to the noise correlation for a given pixel in the two dimensional array is equal to $$\int_{-\infty}^{\infty} \vec{E}_i \cdot \sigma \cdot \vec{E}_j dz.$$

$\sigma$, because of the design of the phantom, is a function of position in the XY plane while being significantly independent of Z over the length of the phantom and is zero outside the phantom. FIGS. 6A–6D show the relative predicted noise correlation basis for coil pairs that have 0, 1, 2 and 3 coils between them. This represents all of the different pairs because of the symmetry of the structure.

Figure 9A:
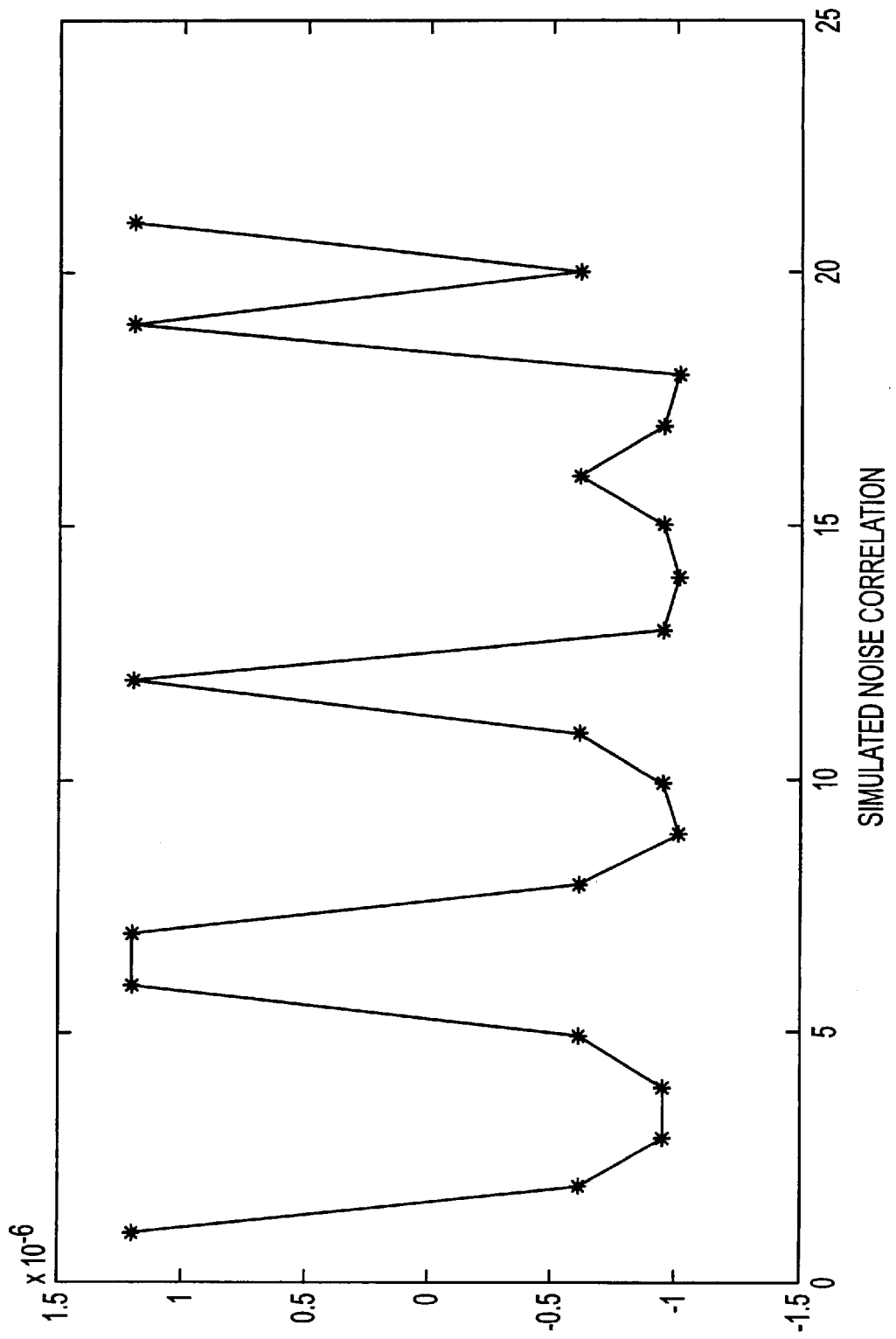
FIG. 9A shows the simulated noise correlation

The noise correlation matrix for the coil array was measured using a Seimens Symphony MRI scanner. This is an eight-channel 1.5T MRI scanner which operates at 63.6 MHz. Because channel 5 was functioning improperly, subsequent calculations were performed, without channel 5, assuming a 7 channel system. FIGS. 9A and 9B show the calculated and the measured values, respectively, for the 21 independent elements of the 7×7 noise correlation matrix when the array is loaded with the constant conductivity phantom. The noise correlation matrix for the phantom in which the 3" ID tube was filled with distilled water was measured for 11 orientations.

FIG. 12B shows that the conductivity map generated from the noise correlation data and MR segmentation data from the MR image shown in FIG. 12A. Details of the subject inversion technique are discussed elsewhere in this application. Both the one-dimensional and the two-dimensional experimental tests have shown that the MR-NT technique can be used to generate an effective relative conductivity map of the sample space. This demonstrates that the noise correlation, which is a function of the overlap of the electric fields within a coil array, can be used to map the conductivity of the sample. The subject MR-NT technique can be extended to three dimensions. The subject technique can have the resolution and speed to generate a high quality map of the conductivity distribution of more complicated samples. Because the MR-NT uses guidance from the MR signal components, which define boundaries, internal boundary locations can be used for improvement of the actual electric fields and thus the noise correlation matrix simulation.

In a specific embodiment, arrays can be utilized which are good MRI coils and also have E-fields at all points in the sample. In another embodiment, coils whose losses are entirely due to conservative E-fields, not local fields associated with components or drive methods can be utilized. The probe array and the individual probes are preferably characterizable, so that all of the signal characteristics can be calculated from the electromagnetic field simulation, the predicted probe and the electronics characteristics, and the assumption about the noise sources. Each probe can be approximately matched to 50 ohms with an average load (similar to how MRI probes are manufactured). A specific embodiment can utilize an array design which can allow for good discrimination of regional noise covariances over the sample region of interest, while maintaining the capability for MR imaging. Similar to the g-factor in parallel detector encoded MRI, a parameter to say how good an array is for an MR-NT measurement can be implemented, such as an "E-factor". The E-factor can be related to the invertibility of the location dependent covariance matrix. The subject array can include motion, for example rotation, that can provide more location information during the exam. This motion will preferably not degrade the standard MRI techniques.

Figure 8:
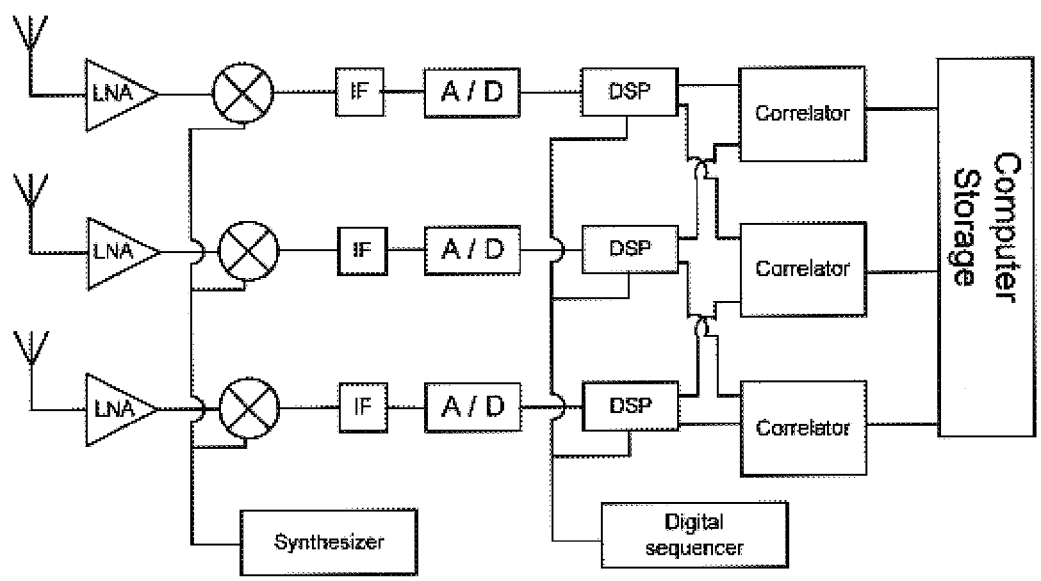
FIG. 8 shows a block diagram of a correlation receiver in accordance with the subject invention.

In a specific embodiment, the subject invention can involve measuring the correlation in the detected noise between different probes within an array of RF probes. The subject method can include digitally mixing the noise signals detected on each channel between each pair of channels. This can involve amplifying and filtering the signal from each channel, digitizing the signal using an A/D converter, and then digitally filtering, processing, multiplying and re-filtering the signal from each pair of channels. A block diagram of the electronics for a specific embodiment is shown in FIG. 8.

Referring to the block diagram, each probe in the array can be attached to a separate narrow band Low Noise Amplifier (LNA), downconverter, If amplifier, and Analog to Digital converter (A/D). This can allow the frequency of operation to be easily changed simply by changing the frequency of the Local Oscillator attached to the down converter. The Digital Signal Processor can be used for filtering, downconverting, and as a quadrature splitter. Digital technology makes it possible to easily experiment with different filter types and bandwidths. The subject method can also maintain uniformity in phase shift and signal amplitudes between channels An image reconstruction algorithm can be used for converting the acquired noise correlation data to an image. The characteristics of the subject probe, the array designs, and the conversion algorithm are mutually dependent. The subject algorithm can enable segmentation and conductivity inversions. In a specific embodiment, the subject method can incorporate information from boundary definition (and E-field continuity equations) and B1 sensitivity maps into the technique for inversion.

In a specific embodiment, an array designed for imaging a single breast can be designed to be integrated with the MRIDC interventional breast patient support. The array can operate with approximately a 100 kHz bandwidth in the frequency between 5 and 100 MHz. The subject array can be rotatable and translatable allowing good signal to noise throughout the sample and high resolution. This can allow the use of larger probes, for better sample coupling, within the array while still maintaining the resolution obtainable with greater number of smaller probes. A specific array can use three rings of eight probes each, with a total of 24 probes and can generate a three-dimensional image.

In a specific embodiment, the subject MR-NT apparatus can first provide the measured noise correlation and MRI image of FOV (field of view).

The subject method can then utilize a computer algorithm to reconstruct a conductivity-distribution map from the available information. Preferably, the subject computer algorithm can efficiently reconstruct a high quality conductivity-distribution map.

A specific embodiment of the subject algorithm can be based on the following formula:

$$M_{ij}(\Omega) = \int_\Omega \vec{E}_i(\sigma, x) \cdot \sigma(x) \cdot \vec{E}_j(\sigma, x) dx \qquad 1)$$

Where $M_{ij}(\Omega)$ is the measured Noise Correlation generated by two probes. $\vec{E}_i$, $\vec{E}_j$ are the electric fields resulting from the two probes at the point x in space and $[\pi(x)]\sigma(x)$ is the conductivity at the point x in space.

In a specific embodiment, the following approximations can be made:

Different objects have different conductivity. Each object has relatively constant conductivity. This approximation seems reasonable because the electrical resistivities of different body tissues varies widely from 0.65 ohm m for cerebrospinal fluid to 150 ohm m for bone [EIT]. Relative impedance of tissues is generally related to the water and electrolyte content in the tissue [Electro].

Conductivity is isotropic. This approximation seems reasonable for tissues when the object size is smaller than or equal to the size range of clinically different tissues in the sample.

There are relatively high contrasts between different objects on MRI image. One object has relatively homogeneous intensity on MRI image. Because protons in different types of tissue relax at different rates, images of different intensity for the different zones can be produced.

Utilizing these approximations, and Simulated Noise Correlation, the relative conductivity map can be generated by the following steps:

Accurate structure determination by segmentation of MRI image. The knowledge of locations of constant conductivities can be provided by this step.

Using Measured Noise Correlation, knowledge of E-field at locations of those constant conductivities, and equation 1), a constrained linear equation system, with constant conductivities as unknowns, can be constructed.

This system can be solved to find the value of those constant conductivities. With the knowledge of the location of those constants, the relative conductivity map can be produced.

This method can involve the following tasks:
structure determination of a given image,
measurement of Noise Correlation,
simulation of E-field of each coil with the help of MRI, and
steady solution of a constrained linear equation system.

These tasks can be solved step by step. The subject approach, which can solve an MR-NT inversion problem step by step, can be referred to as SMSS (Segmentation, Measurement, Simulation and Solution).

In a specific embodiment, Segmentation and Solution can be solved in one step. For example, an approach based on Modified Mumford Shah model and multiphase level set method can be utilized. A specific embodiment of the subject approach can be referred to as MMSMLS (Modified Mumford Shah model and Multiphase Level Set method).

An image reconstruction technique commonly referred to as tomography, can pertain to a technique for imaging 2D cross sections of 3D objects from 1D slices. In other words, the goal of tomography is to reconstruct object profiles and extract object features given a set of tomographic measurements. Mathematically, tomography is recovering (at least approximately) the values of a function from (possibly approximate and/or possibly weighted) an integral of the function over some subset of its domain.

From a mathematical point of view, tomography is an inversion problem. Inversion problems have long been a significant area of research in mathematics, as seen in thousands of publications. The solution to an inversion problem can involve PDE (Partial Differential Equations), differential geometry, measurement theory, numerical analysis, algebra, and so on.

Some excellent algorithms have been found and applied in the field of tomography and can be utilized with respect to the subject invention. A discussion of some of these algorithms will now be discussed. Among the most popular are the Filtered Backprojection Method (FBP), Algebraic Reconstruction Technique (ART), circular harmonic algorithms, Direct Fourier Reconstruction, Tikhonov regularization, total variation method, Ordered Subsets Expectation Maximization (OS-EM), Bayesian reconstruction, and the Layer Stripping Method.

Initially, the exactly correct simulated noise correlation basis is unknown. Secondly, the measured noise correlation may include sources that have not been included in the approximation. Finally, limited noise correlation information can be provided by the hardware system. For these reasons, the tomography problem can be unstable.

Filtered Backprojection (FBP) can be utilized with respect to the subject invention, and is an important algorithm in 2D tomography. This algorithm is essentially a numerical implementation of the Radon inversion formula. However, simple approaches avoiding singular integrals may be used. The Fourier transform is used here for filtering. [CZ], [CH], [CC], [A.M.C 1], [A.M.C 2], [S.R.D.], [DTC], [DC], [EH]

The FBP method is widely used in 2D tomography applications. For CT, FBP is the standard reconstruction algorithm. For PET [LQ1] [HL], the reconstruction method most commonly used is the FBP algorithm. However, reconstructed PET images can suffer from very annoying stripe-like artifacts.

Barber and Brown [BB1] initially developed the FBP approach (which is based on an analogy to the CT reconstruction problem) for EIT. In most cases, this technique has been used to generate dynamic images of the body and display the effects of a change in the electrical properties of the body under two specific conditions. [BHDCAD] [KY]

The subject method can utilize direct Fourier reconstruction, for example with the following reconstruction steps:

perform a 1D Fourier transform on the known integral of the unknown function;

interpolate the Fourier data to a Cartesian grid, using a fast Fourier transform (FFT), invert the interpolation (of the previous step) to obtain the unknown function.

The numerical implementation in a discrete setting is quite intricate. [H.J.N] [SL]

Newton's Method [KR] can be utilized with the subject invention and is intended to minimize the difference between two values, which is sometimes termed as the "objective function." The minimization is achieved by obtaining the derivatives of the objective function. This derivative is assigned to zero, which corresponds to a local minimum of the objective function. A system of equations is therefore generated which, when solved, will give the closest approximation of the actual image in the least-squares sense.

With Newton's Method, if only one step is used, the initial derivatives based on the uniform distribution may be obtained analytically, and need not be recalculated. The algorithm based on one step of the above method can be termed NOSER. The use of Newton's method for more than one iteration requires a considerable amount of computing time. An iterative algorithm, POMPUS [KWM], was developed by Paulson. This method greatly reduces the time needed to produce images and hence considerably eases the problem of performing iterative reconstruction in real-time.

Other methods besides NOSER and POMPUS can be utilized with the subject invention such as: the perturbation method, the Newton-Raphson iteration scheme, the non-linear conjugate gradient (CG) algorithm, which are also based on Newton's Method.

In EIT, because the number of electrodes will, in practice, always be finite, the full Neumann-to-Dirichlet map will not be available, and the inverse conductivity problem becomes effectively ill posed. Therefore, some form of regularization has to be imposed.

The generalized Tikhonov regularization methods have been popular in the solution of many inverse problems and can be utilized with the subject method. One smooth term is added in the energy functional for regularization. The advantage of these methods is that a unique and smoothed solution can be derived. A drawback of the Tikhonov regularization is that it tends to blur edges in reconstructed images. [KN 1], [KN 2] [VVKSK]

The Total Variation method is just a modified version of Tikhonov regularization and can be utilized with the subject invention. The only difference is that the smooth term is changed from squared to absolute value. However, this change overcomes the drawback of Tikhonov regularization, and is well known for its better edge-preserving property. [VO] [BG]

The Layer Stripping method was first described by Cheney et al [MD] and can be utilized with the subject method. This technique is unusual in that it reconstructs images from the periphery inward. It is claimed that for EIT, this method achieves a more accurate conductivity contrast than other methods. This is based on the idea of first finding the electrical parameters on the boundary of the body, then mathematically stripping away this outermost known layer. The process is then repeated, and the medium is stripped away, layer-by-layer, with the electrical parameters being found in the process. This method is appealing because it is fast, addresses the full nonlinear problem, and works well on continuum-model synthetic data. There are examples that this method is successfully used in CT and EIT.

A variety of statistical methods which can be utilized with the subject invention will be discussed. The Ordered Subsets Expectation Maximization (OS-EM) algorithm is used to estimate the probability density of a set of given data. It is used in Image reconstruction by maximizing an objective function (the log-likelihood). Despite the quality of images over the traditional Fourier-based method, the Expectation Maximization iterative algorithm is not typically used due to the tremendous processing time. The use of Ordered Sets (OS) accelerates convergence by a factor proportional to the number of subsets. OS-EM algorithm is an extremely fast and efficient method to accelerate iterative SPECT and PET reconstruction with speed-up factors of close to half the number of projections. Hence, it is rapidly becoming the standard reconstruction method in nuclear medicine.

Based on the assumption that the emission data are the realization of an independent Poisson distributed random vector, it has been widely used in emission and transmission CT, SPECT and PET. [T.K.M] [A.P.D] [J.A.B]

Bayesian reconstruction forms a powerful extension of the maximum likelihood reconstruction method. Bayesian reconstruction methods allow the incorporation of prior information (such as smoothness constraints or partial specified topological information) and therefore further reduce the noise sensitivity. [S.K]

Maximum A Posteriori (MAP) [LQ1] [LQ2] reconstruction methods for 2D and 3D PET systems is based on a Bayesian formulation. These methods combine accurate modeling of the coincidence detection process with statistical priors on the PET images.

With respect to algorithms applicable to medical NT, the model of an object created in the pre-processing stage affects the flexibility of the algorithm that impacts the whole reconstruction process. Accuracy and speed are mainly affected by numerical code implementations. After a satisfactory solution is obtained, the visual representation of the reconstructed image, in a medically useful format, should not be overlooked. Visualization characteristics in the post-processing stage often depend on the initial model and the reconstruction algorithm used. Therefore, the major requirements for algorithms applicable to medical NT include:

Flexibility: Accurate modeling of complex 2D and 3D geometries. Easy application to different probe types.

Accuracy: Usage of high-quality domain discretization. Robustness with respect to noise. Minimal influence of algorithmic constraints on solution accuracy. Suitable algorithm for the problem's non-linear nature.

Speed: Application of sparse matrix storage schemes and solver techniques. Algorithms with problem-adaptive mesh density. Parallelization of code.

Visualization: Extraction of medically significant features from the image. Display of slices, surfaces and volumes.

Like EIT, the subject NT method is distinct from other tomographic techniques. The reconstruction phase is complicated by the fact that the integral of the unknown function is not confined to a narrow beam, as with collimated gamma or X-radiation. The integral spreads out over the entire region to be imaged. The reconstruction method, therefore, is more difficult to implement and more prone to error.

Mathematically, the NT reconstruction problem can be characterized as a nonlinear, ill-posed inverse problem, with many unknowns. The ill-posed aspect of the problem implies that a small variation in the measurements can have a large effect on the reconstructed image. To obtain a stable reconstruction algorithm, a priori information has can be added or regularization techniques can be applied.

In various specific embodiments, the Algebraic Reconstruction Technique (ART), CG algorithm, and/or Total Variation Method can be utilized with the subject noise tomography method.

The subject method can determine the conductivity of a sample via Noise Tomography, based on the following formula:

$$M_{ij}(\Omega) = \int_{\Omega} \vec{E}_i(\sigma, x) \cdot \sigma(x) \cdot \vec{E}_j(\sigma, x) dx$$

where $\vec{E}_i$, $\vec{E}_j$ are the electric fields resulting from the two probes at the point x in space and when the two probes are driven by a unit source, where σ(x) is the conductivity at the point x in space σ(x) can be a complex conductivity tensor.

In a specific embodiment, the subject method can involve mesh generation and simulation of noise correlation. An approximate simulated Noise Correlation basis can be determined with respect to the forward problem in the subject noise tomography method.

The data can then read and analyze data in order to compute the measured Noise Correlation accurately. The subject method can then construct and implement a mathematical model to reconstruct the image, with respect to the inverse problem in the subject noise tomography method.

In a specific embodiment, segmentation can be utilized, i.e. identification of meaningful image components. Segmentation of MRI is a hot topic in Medical Image Processing field. Many approaches have been introduced ([BHC] [CVCHV] [ZD]) and can be incorporated with the subject invention. Provided the assumption that there are relatively high contrasts between different objects on an image, such as MR image, and one object has relatively homogeneous intensity on the MR image, multiphase level set using the Mumford and Shah model [VC] can be utilized to solve this problem. This approach can be totally automatic. Computational costs can be minimized. This approach can work in general cases, with no prior information needed. This approach works even if the initial image is very noisy. There is no need to smooth the initial image. This approach can work for blurred image. No boundaries defined by gradient is required. This approach can produce well-defined segmented objects. No overlap or vacuum phases can be produced. This approach can be easily extended for any dimension images.

However, besides corruption by noise, the brightness of MR image data is often deficient due to Radio Frequency (RF) field inhomogeneities. Hence, some processes may be incorporated before segmentation.

Such preprocessing can include removing signal intensity inhomogeneity by using sensitivity map [KPKWBMJ] [SFN][WGM], which are herein incorporated by reference. The formula $$I = \frac{M}{S}$$

can be used, where I is the true homogeneous image, M is the measured inhomogeneous image, S is the coil sensitivity map. Simulated sensitivity map can be generated with the information of the coil. Then the actual sensitivity map can be deduced by adjusting the simulated sensitivity map with the information of, for example, the MR image. Sensitivity maps are commonly acquired now on most new MR systems to permit parallel acquisitions.

Multiphase level set with Mumford and Shah model can be applied in the subject method to do segmentation. In the general 2D case, the problem can be solved using only two level set functions, and no prior information of how many conductivity-levels the image has is needed [VC]. The idea is based on The Four-Color Theorem. Hence four-phase piecewise smooth model of Multiphase level set with Mumford and Shah is enough for the general 2D case.

Energy functional of four-phase piecewise smooth model for a two-dimensional Image is $$E(u, \Phi, EM) = \int_\Omega |u^{++} - u_0|^2$$

$$H(\phi_1)H(\phi_2)dxdy + \int_\Omega |u^{+-} - u_0|^2 H(\phi_1)(1 - H(\phi_2))dxdy$$

$$\int_\Omega |u^{-+} - u_0|^2 (1 - H(\phi_1))H(\phi_2)dxdy +$$

$$\int_\Omega |u^{--} - u_0|^2 (1 - H(\phi_1))(1 - H(\phi_2))dxdy +$$

$$\lambda_1 \int_\Omega |\nabla u^{++}|^2 H(\phi_1)H(\phi_2)dxdy + \lambda_1 \int_\Omega |\nabla u^{+-}|^2$$

$$H(\phi_1)(1 - H(\phi_2))dxdy + \lambda_1 \int_\Omega |\nabla N^{-+}|^2 (1 -$$

$$H(\phi_1))H(\phi_2)dxdy + \lambda_1 \int_\Omega |\nabla u^{--}|^2$$

$$(1 - H(\phi_1))(1 - H(\phi_2))dxdy +$$

$$\lambda_2 \int_\Omega |\nabla H(\phi_1)| + \lambda_2 \int_\Omega |\nabla H(\phi_2)|$$

Where
$u_0$ is the input image
$\phi_1$ and $\phi_2$ are two level sets
$H(\bullet)$ is the Heaviside function $$u(x, y) = \begin{cases} u^{++}(x, y), & \text{if } \phi_1(x, y) > 0 \text{ and } \phi_2(x, y) > 0 \\ u^{+-}(x, y), & \text{if } \phi_1(x, y) > 0 \text{ and } \phi_2(x, y) < 0 \\ u^{-+}(x, y), & \text{if } \phi_1(x, y) < 0 \text{ and } \phi_2(x, y) > 0 \\ u^{--}(x, y), & \text{if } \phi_1(x, y) < 0 \text{ and } \phi_2(x, y) < 0 \end{cases}$$

is the smoothed and segmented MR image $\lambda_1$ and $\lambda_2$ are two parameters to balance smooth and segmentation.

The first 4 terms are for minimizing the difference between segmented image and the original image. The next 4 terms are local smooth terms, used to smooth the segmented image. The 9th and 10th terms are used to smooth the boundary of each component.

After the above step, several level set phases can be produced. It is possible that one level set phase contains several objects. To identify different objects in one level set phase, union-find algorithm [RS] can be used here to identify connected area in each level set phase. If two areas are disconnected in one level set phase, then they are treated as two different objects. A very small object will be merged with a neighbor with similar intensity.

FIGS. 13A–13D display one example of segmentation of MRI by using the multiphase level set approach. FIG. 13A is the original MRI image, FIG. 13B to FIG. 13D are level set phases based on the image intensity.

The level set method has been proved to be successful for 3D-segmentation problem [BB2] [CV][DMRS] [KSG] [HBG] [MBZW] and can be utilized with respect to the subject invention. Multiphase level set with Mumford and Shah model can be directly extended for 3D-image. In most cases, the energy functional of four-phase piecewise smooth model is still viable since it is rare that many different organs accumulate together.

In case that the 3-D input data is real 3-D, energy functional of four-phase piecewise smooth model can be extended by just changing level set phases $\phi_1$ and $\phi_2$ to 4-D. More level set phases may be needed in case the geometry is really complicated.

In a specific embodiment where the 3-D input data is given by slices, then several steps can be implemented.

The slices can be registered to avoid or reduce, errors caused by movement. Real 3-D data can be generated by interpolation. An extended energy functional of four-phase piecewise smooth model can be applied to real 3-D data.

Another step can include determining the accurately measured Noise Correlation (M). The data read from the hardware system is "noise." For n coils, there are n noise matrices. To compute the noise correlation, the covariance of the noise matrices can be used. In a specific embodiment, several sets of measured data can be collected for each image and the mean of the covariance for all sets of collected data was used as the noise correlation. M can be used to denote all noise correlation.

The calculated covariances can differ from the measured values because of uncorrelated noise from electronics, gain differences, and channel crosstalk. Therefore, for each experiment, S (scale term) and C (constant calibration term) must be computed to calibrate the input data. In order to obtain S and C, several different constant objects were placed, separately, into the coil to determine M. ||RX−(SM+C)|| was minimized with respect to X, S and C. In this expression, S is a constant number and C is a constant vector. Since constant objects were placed in the coil, then X was a constant number for each object. R was the simulated noise correlation basis. S and C kept the same value for each object. Knowing the simulated R and Measured M, the scale term S and calibration term C for the experiment can be found by minimizing ||RX−(SM+C)|| with respect to X, S and C. M will now be referred to as the expression S*Measured data+C.

Simulation of the E-field of a given coil can be accomplished using the appearance of MRI, in order to determine the approximate simulated Noise Correlation basis (R).

With respect to mesh generation, in order to generate a grid, the region under investigation can be parameterized. In a specific embodiment, the unit of measure can be a cube, since it is easy to implement. But in fact, there are many ways to generate mesh, and some are better than using a cube.

Two distinct meshes for the same problem can be introduced in this step. This is an attempt to reflect the fact that actual measurements take place in the 'real' measurement volume, while the noise correlation basis is calculated in a 'simulated' model volume. Therefore, a certain model inaccuracy with respect to the real noise correlation typically exist.

In the general case, the simulation of the E-field is very complicated. In a specific embodiment, two assumptions can be made:

The region under investigation has constant conductivity.
The E-field is uniform in each small unit for the convenience of the numerical application.

Finally, the formula for the E-field can be expressed as:

$$d\vec{E} = \frac{d(\vec{I} * \text{vol})}{\text{dist}}$$

where "dist" is the distance from one point on the coil to the object pixel, "I" is the current at the coil point, and "vol" is the volume of the object pixel.

The simulation of the Noise Correlation basis can be based on the simulated E-field. Each pair of coils can generate one 3D noise correlation matrix. Therefore, if there are n coils, n(n−1)/2 3D noise correlation matrices can be generated. To produce a 2D image, the sum of the 3D noise correlation matrix along the length of the phantom can be used. To produce higher resolution images, the coil can be rotated several times for one image. In the case of 8 coils, 28 equations can be generated for each rotation. The following formula, $$R_{ij}(x, y,) = \int_L \vec{E}_i(x, y, z, \sigma) \cdot \vec{E}_j(x, y, z, \sigma) dz$$

can be used to calculate the noise correlation basis at each 2D pixel, where "L" is the line at (x, y) along the length of the phantom, "i" and "j" are for coil, or prove, "i" and coil, or probe, "j". For numerical implementation, each $R_{ij}$ is a 2D matrix. "R" is used to denote the set of all $R_{ij}$.

By the above steps, the information of position of objects, measured Noise Correlation and simulated Noise Correlation Basis is available. With the known information, an equation system can be constructed.

$$\sum_{k=1}^{n} \sigma_k \int_{\Omega_k} R_{ij} dx dy = M_{ij}$$

where n is the number of objects
$\Omega_k$ is the area of object k
$\sigma_k$ is the relative conductivity of object k
$R_{ij}$ is the Simulated Noise Correlation Basis of Coil i and Coil j
$M_{ij}$ is the Measured Noise Correlation of Coil i and Coil j Since relative conductivity is always non-negative, constraint $\sigma_k \geq 0$ can be added.

In most of the cases, this is an over-determined linear system with constraints. The trust region method introduced in [CL] can be, and incorporated herein by reference, used here to solve this constrained linear system.

This model is based on Muniford Shah model, Multiphase Level Set method and Noise Correlation formula $$M_{ij}(\Omega) = \int_\Omega \vec{E}_i(\sigma, x) \cdot \sigma(x) \cdot \vec{E}_j(\sigma, x) dx.$$

Using this model, the following items can be minimized:
the difference between measured noise correlation and computed noise correlation, the computed noise correlation is generated by solving the forward problem;

the difference between segmented MR image and original MR image
the gradient of each piece on segmented MR image (each piece is for one or more segmented objects) with the purpose being to smooth and denoise the MR image, and
length of edges of all objects the purpose is to make the edge smooth).

Multiphase Level Set can be used here to smartly describe different image pieces and objects edges.

Define $\Omega$: The region of interest n—upper bound of the number of objects, which is given as a prior information m—the number of level sets, m=log"$_2$ $H(\Phi) = (H(\phi_1), \ldots, H(\phi_m))$—The Vector Heaviside function $$H_\varepsilon(z) = \frac{1}{2}\left(1 + \frac{2}{\pi}\arctan\left(\frac{z}{\varepsilon}\right)\right), \varepsilon$$

here is a small positive number as parameter $\Phi = (\phi_1, \ldots, \phi_m)$—The Vector level set function $\chi_1$—Characteristic function for each class I, $1 \leq I \leq n$ $X_1$—Relative conductivity for each class I, $1 \leq I \leq n$ Definition of $\chi_1$ and $X_1$ is as follows In case, there are 9 phases, 3 level set are needed to describe those 9 phases. Use $\chi_{ijk}$ and $X_{ijk}$ to denote $\chi_1$ and $X_1$, i is for $\phi_1$, j is for $\phi_2$, k is for $\phi_3$. i,j,k can only be 0 or 1, 1 means H, 0 means 1−H. Hence $\chi_{111} = H(\phi_1)H(\phi_2)H(\phi_3)$ $\chi_{011} = (1 - H(\phi_1))H(\phi_2)H(\phi_3)$ and so on.

$X_{111}$ is the mean conductivity of area $\phi_1 > 0$, $\phi_2 > 0$, $\phi_3 > 0$ $X_{011}$ is the mean conductivity of area $\phi_1 < 0$, $\phi_2 > 0$, $\phi_3 > 0$, and so on.

u—Original MRI image $u_1$—the segmented MR image for class I, $1 \leq I \leq n$ Parameters $\lambda_1, \lambda_2, \lambda_3$—trade off between terms Then the energy function is:

$$E(X_I, u_I) = \left\| \sum_{1 \leq I \leq n = 2^*} X_i * \int_\Omega R\chi_i dA - \overline{M} \right\|_2^2 + \lambda_1 \sum_{1 \leq I \leq n} \int_\Omega |\nabla H(\phi_i)|$$

$$+ \lambda_2 \sum_{1 \leq I \leq n = 2^*} \int_\Omega |\nabla u_i|^2 \chi_i dx dy + \lambda_3 \sum_{1 \leq I \leq n = 2^*} \int_\Omega |u - u_i|^2 \chi_i dx dy$$

This model can solve the tomography problem with reference images. It is simultaneously capable of:
reconstruction of conductivity distribution map,
segmentation for both reference and reconstructed images, and
denoising referenced MR image.

This model can be extended for 3-D image by simply changing level set phases to be 4-D.

In a specific embodiment, a Modified Mumford-Shah by Level Set (MMSLS) can be utilized. This step can be used to construct mathematical models and implement them in order to obtain conductivity distribution (reconstructed image). A novel model for image reconstruction, based on the Mumford-Shah model and Level Set, is introduced here:

$$\min_{\sigma,k,ER,EM} E(\sigma, k, ER, EM) = \min_{\sigma,k,ER,EM} \left( \int_{\Omega\setminus k} |\nabla \sigma| dx + \lambda_1 \left\| \int_{\Omega} \sigma(R+ER) dx - (\vec{M}+\vec{EM}) \right\|_2^2 + \lambda_2 |k| + \lambda_3 \|EM\|_2^2 \right)$$

where

ER is the perturbation of R,

EM is the perturbation of M, k is a closed subset of $\Omega$, representing the union of object boundaries, Parameters $\lambda_1$, $\lambda_2$, $\lambda_3$ are trade off between terms, the first term relates to smoothness of reconstructed image, the second term relates to minimize RX−M with considering error and noise of R, M, the third term relates to minimize the length of curves, to keep the curves smooth, and the forth term relates to minimize EM.

Since EM is just noise, it should be small. In this model, ER was not minimized because it is an error. Better results were obtained without minimizing ER.

Several advanced technologies are used in this model: Mumford-Shah Model, Multiphase Level Set Method, and Total Least Square Method.

Since 1986, the Mumford-Shah model has been widely used in image denoising, image segmentation, and image registration. [CV1] [CV2] [CTTHWG] [TYW] [MKR] [YKKOT] [MS1] [MS2] In the field of Tomography, only one paper has been published [RS] using the Mumford-Shah model for EIT. However their model can only deal with simple cases or must have prior information. In a specific embodiment of the subject invention, a more general model can be utilized, with a better numerical implementation method.

This model is a Modified version of Mumford-Shah Model, and is solved by using Level Set, hence it is called it MMSLS. The following discussion MMSLS for cases ranging from simple to complex.

In the case of MMSLS applied to Binary Field Model several assumptions can be used. It can be assumed that in the region of interest, there are several unknown homogeneous regions with an unknown constant conductivity value of x. It can also be assumed that the background medium is uniform with an unknown constant conductivity value of y. Using these assumptions, the energy functional is:

$$\min_{x,y,C,ER,EM} E(x, y, C, ER, EM) =$$

$$\min_{x,y,C,ER,EM} \left( \left\| x * \int_{\Omega^+} (R+ER) dA + y * \int_{\Omega^-} (R+ER) dA - (\vec{M}+\vec{EM}) \right\|_2^2 + \lambda_1 \int_0^1 |C'(p)| dp + \lambda_2 \|EM\|_2^2 \right)$$

Where C is the evolving curve. Level Set is used here for numerical implementation.

In the case of MMSLS applied to Multiple Intensity Level Set Model, if the number n of different conductivities is known, then, the model can be simplified $$\min_{X,C,ER,EM} E(X, C, ER, EM) =$$

$$\min_{X,C,ER,EM} \left( \left\| \sum_{1 \le l \le n = 2^m} X_l * \int_{\Omega} (R+ER)\chi_l dA - (\vec{M}+\vec{EM}) \right\|_2^2 + \right.$$

-continued $$\left. \lambda_1 \sum_{1 \le i \le m} \int_{\Omega} |\nabla H(\phi_i)| + \lambda_2 \|EM\|_2^2 \right)$$

H—Vector Heaviside function $\chi_l$—Characteristic function for each class I $X_l$—Relative conductivity for each class I Here, multiphase level set framework can be used for numerical implementation. [CV2]

With respect to applying MMSLS to General Case, If no prior information is available, the following model may be used:

$$\min_{\sigma,k,ER,EM} E(\sigma, k, ER, EM) =$$

$$\min_{u,k,ER,EM} \left( \int_{\Omega} (1-v)^2 |\nabla \sigma| dx + \lambda_1 \left\| \int_{\Omega} \sigma(R+ER) dx - (\vec{M}+\vec{EM}) \right\|_2^2 + \right.$$

$$\left. \lambda_2 \left( \frac{\rho}{2} |\nabla v|^2 + \frac{v^2}{2\rho} \right) + \lambda_3 \|EM\|_2^2 \right)$$

Where $v(x) = \begin{cases} 1, & x \in k \\ 0, & \text{otherwise} \end{cases}$ $\rho$ - a fixed number near 0

This model can solve the tomography problem without prior information by using the Mumford-Shah Model. Here, v is an edge strength function that takes its value close to 1 on the edges, and rapidly decays away from the edges to a value of zero in homogeneous regions. [J.S]

If an MRI image is given as a reference, and the conductivity distribution is desired, then the information of the MRI image can be used to obtain better results. For this case the energy function is:

$$\min_{X,C,ER,EM} E(X, C, ER, EM) =$$

$$\min_{X,C,ER,EM} \left( \left\| \sum_{1 \le l \le n = 2^m} X_l * \int_{\Omega} (R+ER)\chi_l dA - (\vec{M}+\vec{EM}) \right\|_2^2 + \right.$$

$$\left. \lambda_1 \sum_{1 \le i \le m} \int_{\Omega} |\nabla H(\phi_i)| + \lambda_2 \|EM\|_2^2 + \lambda_3 \sum_{1 \le l \le n = 2^m} \int_{\Omega} |u - c_l|^2 \chi_l dx dy \right)$$

u—MRI image $C_l$—the intensity average of MRI image in area

This is the first model that solves the tomography problem with reference images. This model is simultaneously capable of:

Reconstruction of conductivity distribution

Segmentation for both reference and reconstructed images

Denoising MRI reference images

Programs utilized in the experiments conducted produced using Matlab, and ran on a Compaq PC with 1 GHz CPU speed. SMSS was used here to generate the conductivity distribution map.

Figure 1A:
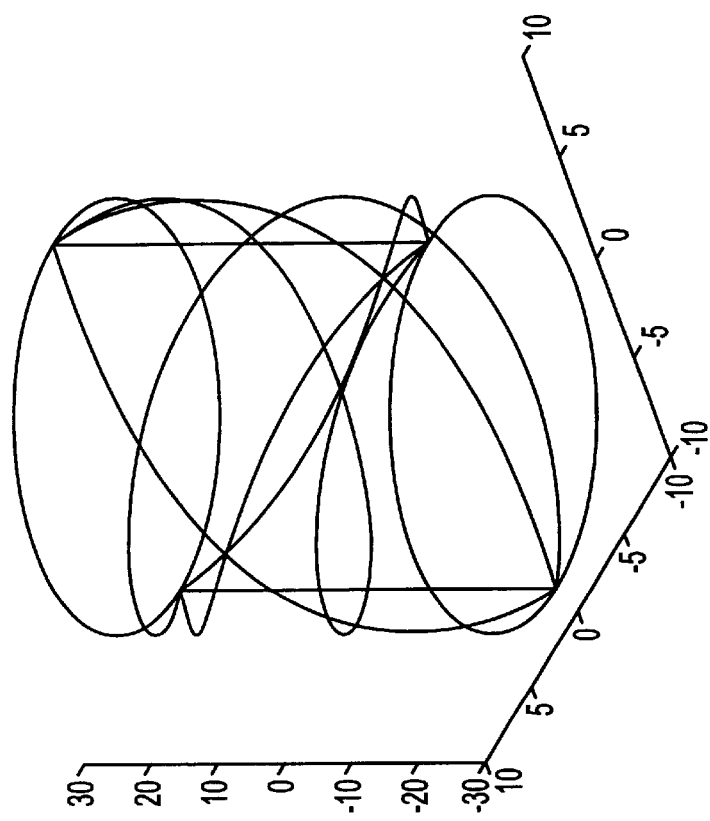
FIG. 1A shows a coil used in a one dimensional experiment, having four spiral birdcage coil legs mounted on a cylinder
Figure 3C:
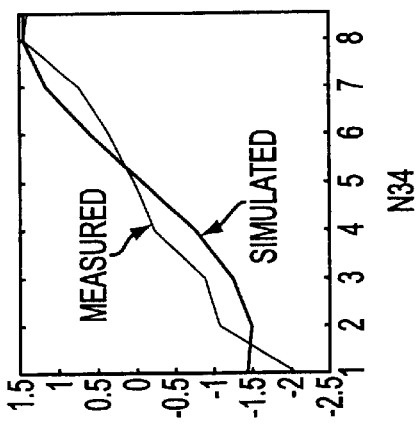
FIGS. 3A–3F show the z-dependence of simulated and measured noise covariances for an experiment in accordance with the subject invention
Figure 3F:
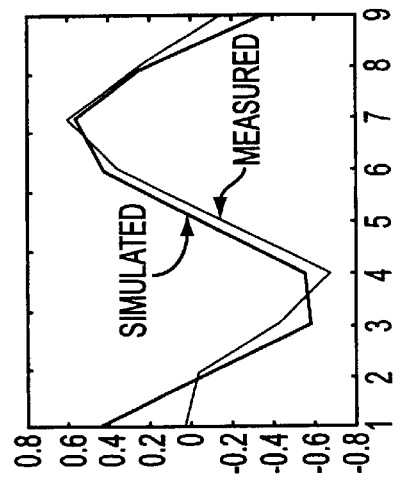
Figure 3B:
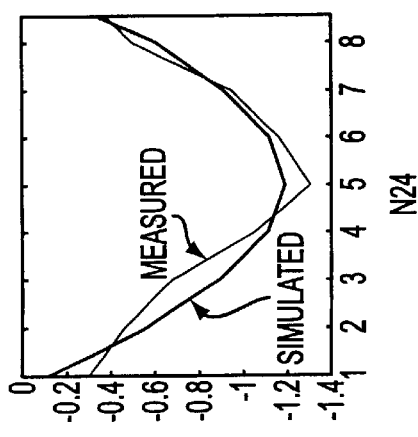
Figure 3E:
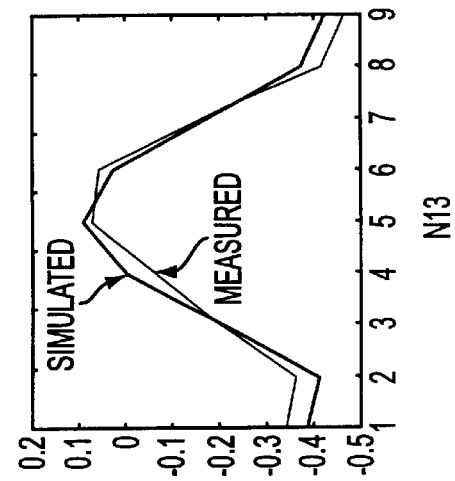
Figure 3A:
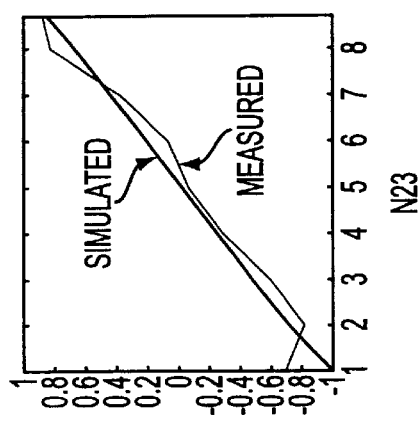
Figure 3D:
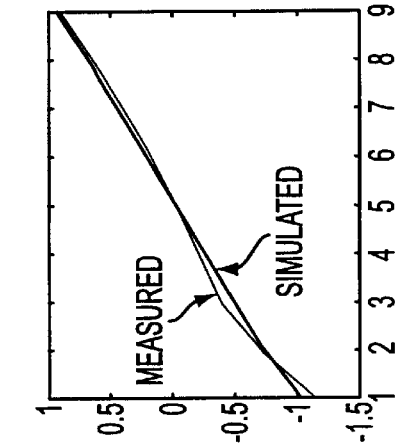

The coil shown in FIG. 1A was used in the one dimension experiment, and included:

4 spiral birdcage coil legs mounted on a cylinder with a diameter of 17.5 cm, and length of 56 cm.

Rotation of the coil legs in degrees were [−180° 0° 180° 360°, respectively]

Mesh generation was accomplished by dividing the smallest box containing the cylinder defined above into 75*75*75 same size small boxes.

The phantom sample used in the experiment was two discs with a diameter of 16 cm and width 10-cm and 5-cm.

Figure 16A:
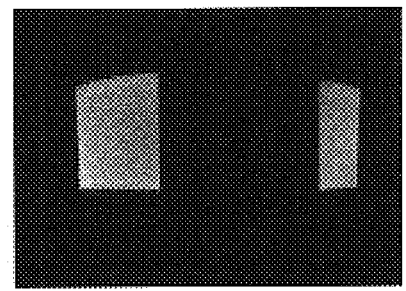

FIGS. 16A through 16C display the segmentation result in this one-dimensional experiment. FIG. 16A is the original MR image. FIG. 16B is the one-dimensional data generated by using the intensity average. FIG. 16C is the segmentation result based on the generated one-dimensional data.

FIG. 11 shows the results of the experiment. The dots show the real relative conductivity distribution, and the curve shows the reconstructed conductivity distribution by using the segmentation result. The unit of x-axis is the centimeter. The result is very close to if not exactly the same as, the real relative conductivity distribution. The CPU time for this reconstruction was 0.26 seconds.

FIG. 1B shows the result of an experiment using MMSLS. A first curve shows where the phantom disc actually is, and a second curve shows the result of using the MMSLS model. The unit of x-axis is the centimeter. By using the real position and disc width, the ideal norm of RX–M is calculated as 28.2831. The resulting norm, using MMSLS, is 33.6771. The CPU time for this reconstruction was 6.875 seconds.

The other idea is to use the coil with no loading, and in that way obtain the noise correlation $M_0$. Consider $M_0$ as the fixed error of this coil. Then, use several different constant objects with known conductivity X to obtain the noise correlation M. Next, compute R by minimizing $\|RX-(M-M_0)\|$. To find the function between ER and conductivity, compare the computed R (CR) and simulated R (SR), where ER=CR-SR. In future computations, this function can be used to calibrate R in the forward problem.

In a specific embodiment, the subject NT technique involves measuring the correlations in the detected noise between different probes within an array of RF probes. In order to accurately and efficiently measure the correlations, the noise signals detected on each channel will be digitally mixed for each pair of channels. This can involve amplifying and filtering the signal from each channel can, digitizing the signal using an A/D converter, and then digitally filtering, processing, multiplying and re-filtering the signal from each pair of channels. The block diagram of the a specific embodiment is shown in FIG. 8. In the block diagram of FIG. 8, each probe in the array is attached to a separate narrow band Low Noise Amplifier (LNA), downconverter, IF amplifier and Analog to Digital converter (A/D). This arrangement allows the frequency of operation to be changed simply by changing the frequency of the Local Oscillator that is attached to the down converter. The Digital Signal Processor is used for filtering, downconverting and as a quadrature splitter. Digital technology makes it possible to easily experiment with different filter types and bandwidths, while maintaining uniformity in the phase shift and signal amplitudes between channel pairs. The correlators then calculate the time average of both the in- and out-phase components of the noise correlation for each channel pair.

The design of modem high-speed A/D converters (Analog Devices Model AD6640) permits sampling rates of greater than 65 MHz. These sampling rates, when combined with a digital quadrature receiver such as the AD6620, allow the final IF mixing to be performed digitally, for an output bandwidth on the order of 1 MHz. This combination of a high speed A/D and a high speed digital receiver makes it possible to maintain the same phase, amplitude and filtering characteristics, even when splitting the signal from each probe into (n−1) correlators. For a specific 24-probe system, the signal from each channel can be split into 23 correlators, for a total of the 276 correlators required for the entire system.

This design should permit a broad detection bandwidth while minimizing data transfer and storage requirements. If data from 24 A/Ds is recorded directly to a disk for processing at a later date, the design becomes quite important. In a 24-channel system, a 500 kHz IF bandwidth per channel requires more than 20 Megabytes per second of storage.

Figure 4A:
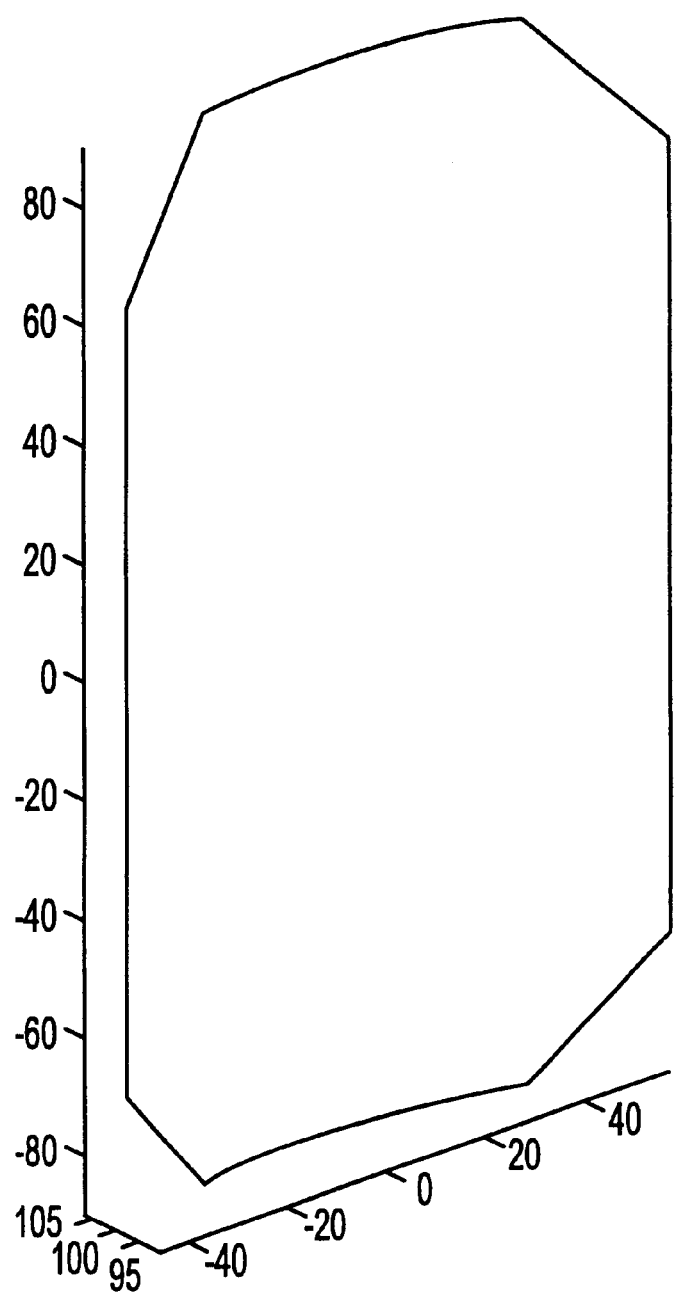
FIG. 4A is an image of one loop of a coil used in a two-dimensional experiment.
Figure 6A:
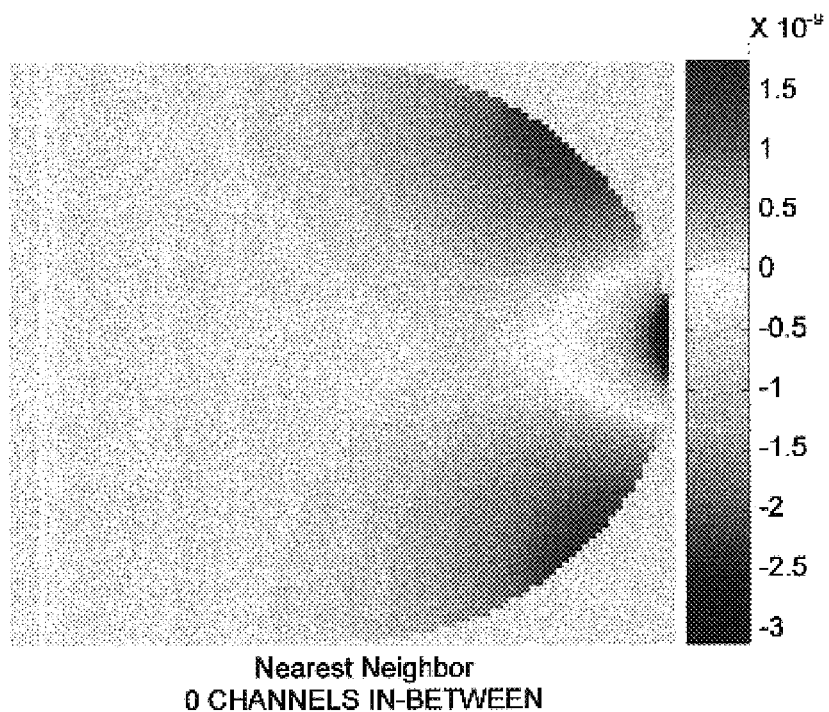
FIGS. 6A–6D show four patterns in the center of the height of the phantom; the near neighbor with 0 channels in-between, 1 channel in-between, 2 channels in-between, and 3 channels in-between, respectively
Figure 6B:
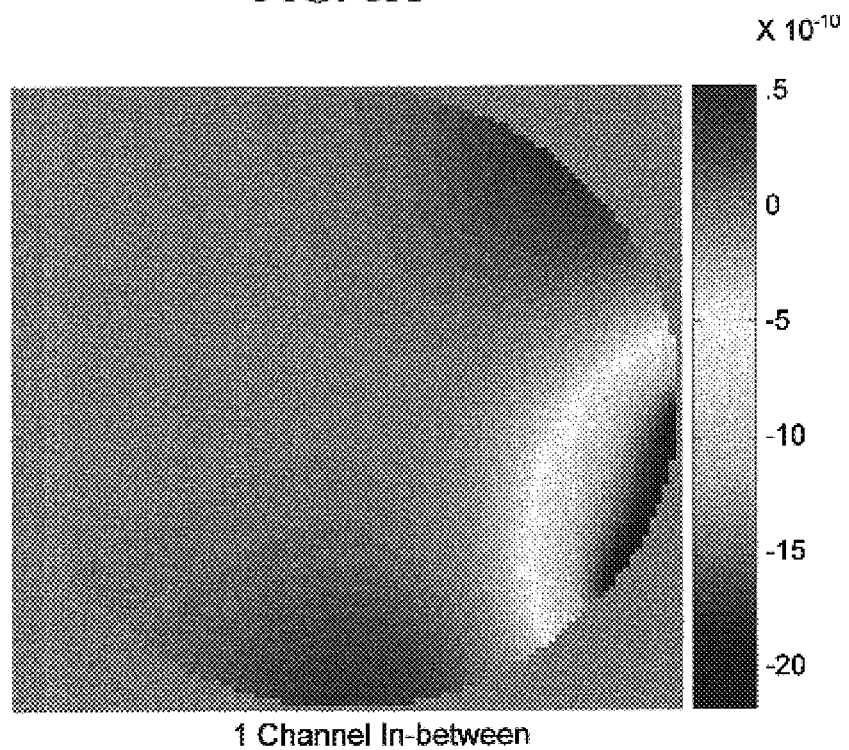
Figure 6C:
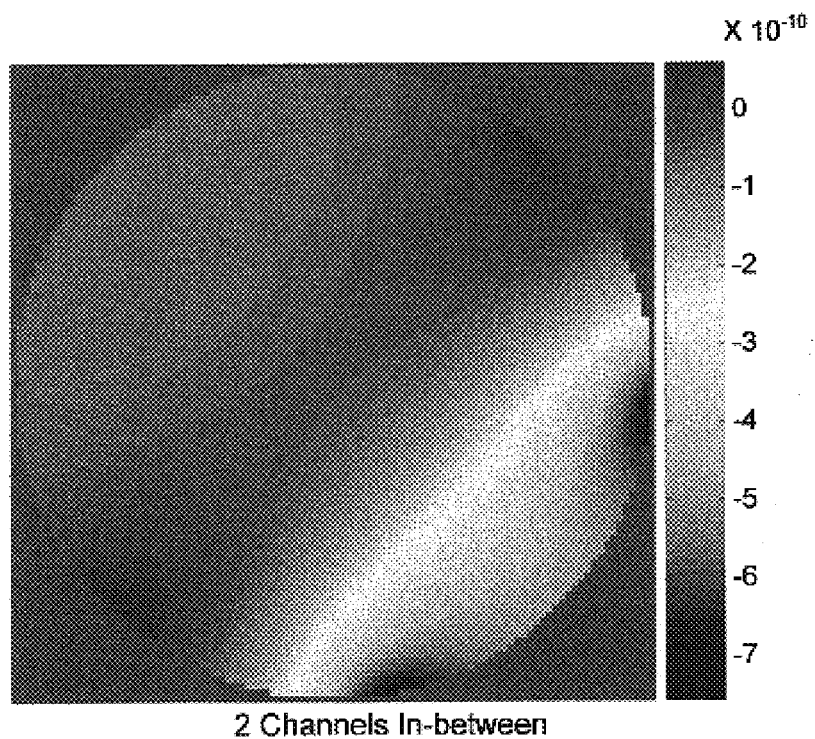
Figure 6D:
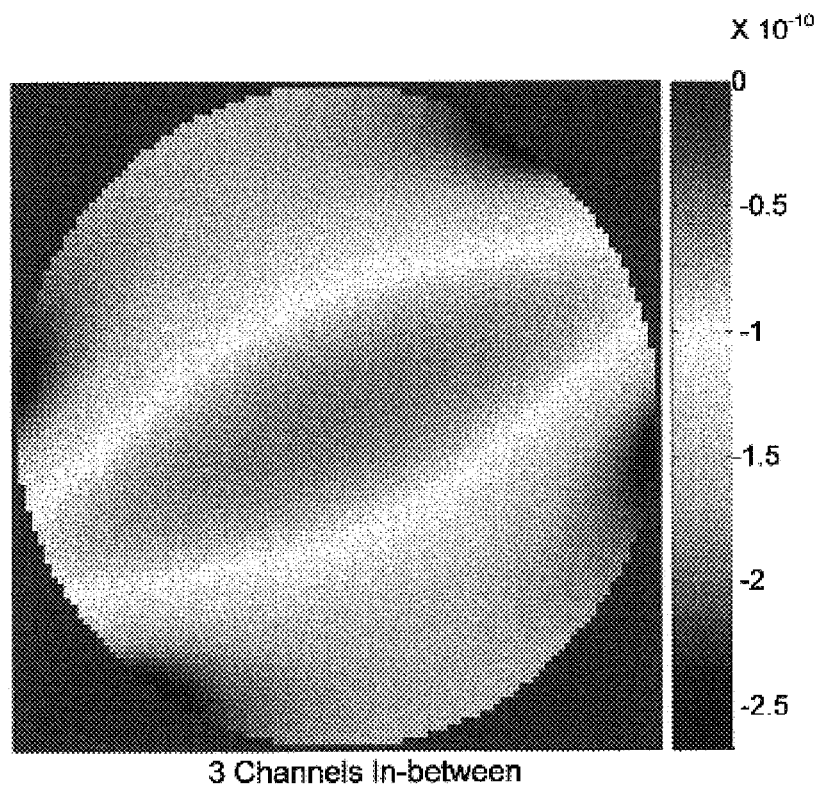

The coil used in a specific two dimensional experiment, included an array having eight resonance tuned loop probes, each loop sweeping an angle of 57 degrees, with a height of 180 mm. The coil array was constructed on a 215.9 mm (8.5") OD Acrylic tube. Each of the coils was overlapped with its nearest neighbors, providing approximately 20 dB of isolation from its nearest neighbors. FIG. 4A is the image of one loop of the coil used in 2D experiment. FIG. 4B is the coil use in 2D experiment.

The mesh is generated by dividing the smallest box, containing the cylinder defined above, into 100*100*100 same size small boxes. For 8 channels, there are 4 patterns generated for the Noise Correlation Basis, which have 0, 1, 2, or 3 channels between them. FIGS. 6A–6D show these four patterns in the center of the height of the phantom.

The phantom used in this two dimensional experiment is constructed of a 197 mm (7.75") ID by 180 mm long acrylic tube that is filled with a solution of $Cu_2SO_4$ (2.0 grams/Liter) and NaCl (4.5 grams/Liter). The conductivity of this solution is on the order of 0.8 S/m. There are three smaller acrylic tubes, each of which is 180 mm long, contained within the 197 mm OD tube. FIG. 5A is the MRI image of the phantom. FIG. 5B is the photo of the phantom.

During the measurement of the measured Noise Correlation, the phantom was rotated 11 times to obtain 11 groups of measured noise correlation. After the pattern of each group of Measured Noise Correlation was plotted, it was found that the resulting pattern was quite different from the simulated pattern. Later, this difference was attributed to a problem with channel 5. After deleting channel 5, the simulated and measured patterns, as seen in FIGS. 9A–9B, became similar.

If the container is ignored, the digitized real image should look like the image in FIG. 7A. Furthermore, if it is assumed that the relative conductivity of distilled water is 0, and the relative conductivity of saline solution is 1, then the norm of RX–M is 1.9712e-006. The reconstructed image (FIG. 7B) has a resolution of 100*100. The norm of RX–M is 1.45e-006. The CPU time is 25 seconds. The solved relative conductivity of saline solution and water is 1.0 and 0.2, respectively. The black dots (around the periphery of the blue area) are the result of automatic segmentation.

The new approach, using MMSLS, is quite flexible. It can be used for any geometry without prior information. Furthermore, this approach has no special coil requirements. Hence it may be easily applied to a variety of coil types.

The MMSLS algorithm has proven itself to provide accurate results. Comparing the two values of the norm of RX–M, as calculated in the previous section (3.5.2.6), the result of the calculation using MMSLS has an error that is 35.96% lower. Moreover, this result was calculated using very limited and noisy data.

Because the MMSLS algorithm is object based, not pixel-based, this approach, for an equivalent output resolution, uses no more than 5% of the time used by traditional regularization methods in the 2D experiment.

Moreover, the reconstructed image, using MMSLS, is smooth, and the edge is perfectly preserved. The visualization is therefore much better than when using other approaches. And mesh generation is no longer crucial, because a finer mesh can be generated with only a small addition to the calculation.

Another impressive advantage of this approach is that it can accomplish segmentation and reconstruction at the same time. Actually, the zero level set is the desired segment. This is a very useful feature in clinical applications.

The model is based on an assumption that a is piecewise constant, i.e., in a small region σ is a constant.

For this special experiment, just one constant object was used to obtain the calibration constants S and C.

A first line in FIG. 9C is the simulated noise correlation (R) without channel 5. A second line is the calibrated noise correlation (M) using S and C. It can be seen that after scaling and calibration, the pattern of R and M are very nearly coincidental.

In this experiment, since the phantom was rotated 11 times, each rotation generated 28 different noise correlation values for a total of 308. But, the deleted data from channel 5 reduced that number to 231. That is to say that there are 231 equations with which to reconstruct the image.

Figure 14A:
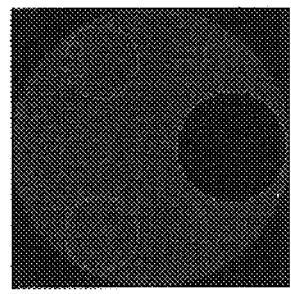
FIGS. 14A–14E show results based on an ideal MR image of a phantom.
Figure 14B:
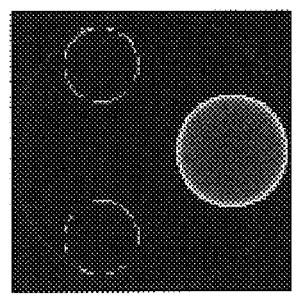
Figure 14C:
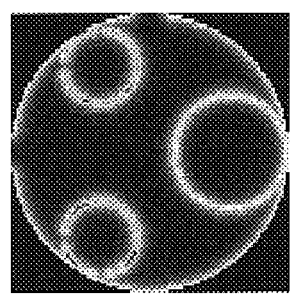
Figure 14D:
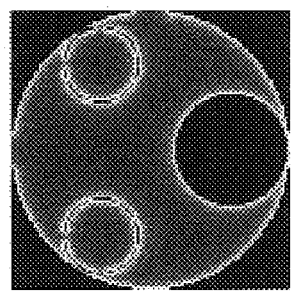
Figure 14E:
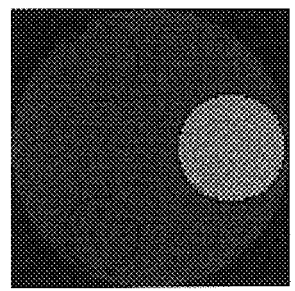

Since there are only several unknowns, only data from rotation 7-10 was used to find the relative conductivity. Area in one level set phase is treated as one object. FIGS. 14A–E display the results based on the ideal MR image. FIG. 14A is the ideal MR Image. FIGS. 14B–14D is segmentation result based on the ideal MR Image. FIG. 14E is the reconstructed conductivity distribution map based on the segmentation result FIGS. 14B–14D. The solved relative conductivity of saline solution, water and plastic is 1.0000, 0.2805 and 0.0399.

Figure 15A:
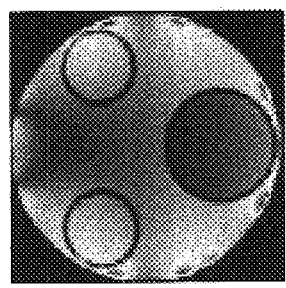
FIGS. 15A–15E show results based on the real MR image of a phantom.
Figure 15B:
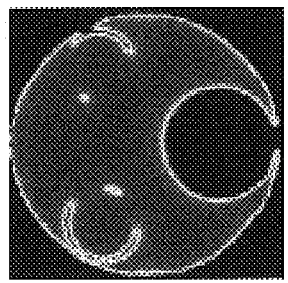
Figure 15C:
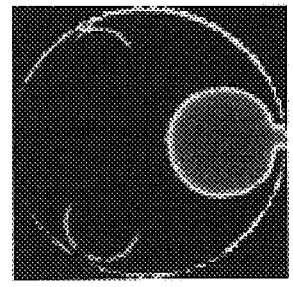
Figure 15D:
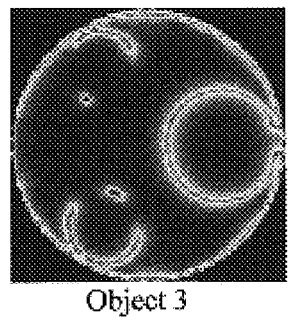
Figure 15E:
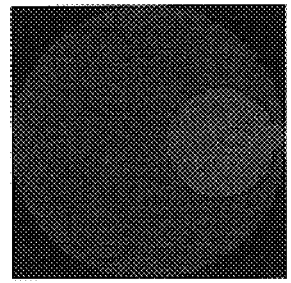

FIGS. 15A–E display the results based on the real MR image of the phantom. FIGS. 3–26 is the real MR Image. FIG. 15A is segmentation result based on the real MR Image. FIG. 15E is the reconstructed conductivity distribution map based on the segmentation result FIGS. 15B–15D. The solved relative conductivity of saline solution, water and plastic is 1.0000 and 0.1873 and 0.1230.

The MR image used here is very inhomogeneous, but the segmentation approach still worked well. If the MR image can be preprocessed to get the ideal MR image, then better segmentation result and conductivity distribution map can be produced.

In addition, the subject approach, using SMSS, is flexible. Since the segmentation approach introduced here is powerful, SMSS can be used for any geometry without prior information. Furthermore, SMSS has no special coil requirements. Hence it may be easily applied to a variety of coil types.

SMSS has proven itself to provide accurate results. By the experiments of one-dimension and two-dimension, the position of objects and relative conductivities are all accurately found.

Because the approach is object based, not pixel-based, it is very fast. For the total process of a 100*100 image, except simulation of noise correlation basis, it takes less than one minute.

Moreover, the reconstructed relative conductivity distribution map is smooth, and the edge is perfectly preserved. The visualization is therefore distinct.

Another impressive advantage of this approach SMSS is that it can accomplish segmentation and reconstruction of relative conductivity distribution map, segmentation, smoothing and denoising for referenced MR image at the same time.

To get a homogeneous intensity MRI image, sensitivity map is needed. Hence SENSE (Sensitivity Encoding for Fast MRI) encoding may be involved in this system.

In short, MR-NT can generate segmented high-resolution conductivity distribution map and segmented MR image that no other imaging modality can provide.

The SMSS model is based on an assumption that σ is piecewise constant, i.e., conductivity is a constant for each object. Because the result of segmentation is influenced by the quality of MR image, the reconstructed conductivity map may be incorrect if with a misleading MR image.

In a specific embodiment, the individual probes can each produce a large electric field within the sample. According to the reciprocity therom the signal detected on the probe for an electric current at a point within the sample will be proportional to the electric field generated by the probe at that point. The subject probe can have a small radiation loss. This will help increase the ratio of sample noise to the other noise sources detected on the probe by decreasing the effects of external noise sources. The noise detected on each probe preferably is dominated by the electronic thermal noise generated with in the sample. The subject NT technique allows determination of the conductivity distribution within the sample by inverting the measured noise correlations that result from the overlap of the electric fields from different probes. The combination of the probe and the array can be designed to help optimize the inversion process. In a specific embodiment, each probe interacts significantly with only its nearest neighbors. In each probe another specific embodiment interacts equally with every probe in the array. The probe array should preferably be designed so that the signal correlation between channels is dominated by the resistive coupling resulting from the conductivity in the sample.

In a specific embodiment, the entire NT probe array and sample can be contained within an RF enclosure in order to reduce the effects of external RF sources. In addition, the RF probe array can be screened.

In order to increase the spatial resolution, the NT RF probe array can be mounted on a rotatable, translatable housing. In a specific embodiment, the prove array can have 4-fold rotational symmetry. Because of the rotational symmetry, the housing can be designed to rotate at least 90 degrees. In another embodiment, an 8-fold rotational symmetry can be achieved and the housing can rotate at least 45 degrees. The design of the housing can have rotational precision and repeatability greater than three degrees and translational precision and repeatability greater than 3 millimeters. In another embodiment, the degree and 1 millimeter can be the precision and repeatability. The motion of the rotation and translation can be synchronized with the experiment. MRI compatible motors will be used with shaft drives to locate the motors some distance from the imaging region. The Integrated Functional Imaging System can be used as the interface platform. This system is compatible with all three of most common 1.5T and 3.0T MRI systems currently, and can be adapted for other systems. The paradigm development and control system can allow synchronization with each phase encode step. Control signals can be readily available for control of motors. Special sequence/paradigms can allow sufficient time is available for motion to occur during "dead" times of the sequence.

In order to calculate the expected electric fields in the sample, it is necessary to know (or measure) the relative locations of each probe. Motion of the probe set with respect to the sample enables multiple tomographic views. It may be advantageous in some cases to move some probes with respect to both the sample and other probes. As long as the motion is controlled and known (or measured), the equations can be solved in a similar way. Another permutation would be to move some probes in a first prescribed way and other probes in a second, different prescribed way. For example, for rotation, one set of probes may be rotated at a different rate than another set of probes.

In 3-D case, considerable-computing time to solve the underlying partial differential equation may be needed. Hence, Adaptive grid techniques can be employed.

MRI can provide image and magnetic field of ROI (Region of Interest). Some techniques integrating EIT into MRI system [OEI1] [OEI2] [KWYK] has been developed to use the magnetic field information and can be incorporated with the subject invention.

The Noise correlation basis is calculated with the simulation of the E-field. However the E-field is simulated with the assumption that the region under investigation has constant conductivity, which may not actually be true. With a referenced MR image, the geometry information of conductivity distribution is available and can be used to get better simulation of E-field.

The simulation of the E-field and noise correlation basis is similar to the forward problem in EIT. The simulation is the calculation of E and R, when the conductivity distribution is a given. The forward problem is extremely important in the iterative method. The solution to the forward problem is required to update R with the updated conductivity distribution. To solve the forward problem for MR-NT, Maxwell equations should be solved.

EXAMPLE 4

Application of Modified Mumford-Shah Model to Noise Tomography

The Noise Tomography method can utilize the following formula $$M_{ij}(\Omega) = \int_\Omega \vec{E}_i(\sigma, x) \sigma(x) \vec{E}_j(\sigma, x) dx$$

$\vec{E}_i$: the electric fields resulting from the probe i at the point x in space $\vec{E}_j$: the electric fields resulting from the probe j at the point x in space σ: the conductivity at the point x in space Ω The region of interest Under assumptions conductivity is a constant for one object electric fields is not influenced much by conductivity distribution The formula above can be simplified as $$M_{ij}(\Omega) = \sum_{k=1}^{N} \sigma_k \int_{\Omega_k} \vec{E}_i(x) \cdot \vec{E}_j(x) dx$$

Where N is number of objects in ROI (region of interesting). The above formula is same as M=RX. Where M is the Measured Noise Correlation. R is the integral of electric field, X is the distribution of conductivity. M can be measured by probe coil, R can be computed by simulation. X can then be found. It can be a challenge to accurately solve the M=RX system. There are at most hundreds of measured noise correlation; but even for a 100*100 image, 10000 unknowns need to be solved. The measured noise correlation itself may not accurate. The subject invention can utilize the object-based method Mumford-Shah model. If the upper bound of number of different objects is known, then the multiphase level set method can be applied.

n—upper bound of the number of objects, which is given as a prior information m—the number of level sets The Vector Heaviside Function $$H(\Phi) = (H(\phi_1), \ldots, H(\phi_m))$$

$$\Phi = (\phi_1, \ldots, \phi_m)$$

$$H_\varepsilon(z) = \frac{1}{2}\left(1 + \frac{2}{\pi}\arctan\left(\frac{z}{\varepsilon}\right)\right)$$

$\chi_1$ Characteristic function for each level set phase I
$1 \leq I \leq n$

The definition of characteristic function can be found in [VC]

$X_1$ Relative conductivity for each level set phase $1 \leq I \leq n$

λ Parameter trade off between terms

Then the energy function of MMSLS is $$\min_{X,\chi} E(X, \chi) = \min_{X,\chi}\left(\left\|\sum_{1\leq l\leq n=2^m} X_l * \int_\Omega R\chi_l dA - \vec{M}\right\|_2^2 + \lambda \sum_{1\leq i\leq m} \int_\Omega |\nabla H(\phi_i)|\right)$$

Phantom Used in Experiment

A phantom is constructed of a 197 mm (7.75") ID by 180 mm long acrylic tube that is filled with a solution of Cu2SO4 (2.0 grams/Liter) and NaCl (4.5 grams/Liter). The conductivity of this solution is on the order of 0.8 S/m. There are three smaller acrylic tubes, each of which is 180 mm long, contained within the 197 mm OD tube. FIG. 5 is the MRI image of the phantom. FIG. 4 is the photo of the phantom.

Result

In this experiment, there are only 231 equations with which to reconstruct a 100*100 image. If the container is ignored, the digitized real image should look like the image in FIG. 5. It is assumed that there are two objects. Furthermore, if it is assumed that the relative conductivity of distilled water is 0, and the relative conductivity of saline solution is 1, then the norm of RX−M is 1.9712e-006.The reconstructed image (FIG. 6) has a resolution of 100*100. The norm of RX−M is 1.45e-006. The CPU time is 25 seconds. The solved relative conductivity of saline solution and water is 1.0 and 0.2, respectively. The black dots (around the periphery of the blue area) are the result of automatic segmentation.

The MMSLS algorithm can provide accurate results. Moreover, because the MMSLS algorithm is object based, not pixel-based, this approach, for an equivalent output resolution, uses no more than 5% of the time used by traditional regularization methods in the 2D experiment.

Moreover, the reconstructed image, using MMSLS, is smooth, and the edge is perfectly preserved. The visualization is therefore much better than when using other approaches. And mesh generation is no longer crucial, because a finer mesh can be generated with only a small addition to the calculation.

This approach is can accomplish segmentation and reconstruction at the same time. Actually, the zero level set is the desired segment. This is a useful feature in clinical applications. A reasonable mesh can reduce computing time (especially in 3D case), increase stability and produce a better-reconstructed image.

In different cases, the parameters used in MMSLS may be different. In a specific embodiment MMSLS parameters can be chosen automatically.

[CV] Tony F. Chan and Luminita A. Vese "Active Contour and Segmentation models using geometric PDE's for medical imaging" UCLA CAM Report 00-41, 2001.

[VC] L. A. Vese and T. F. Chan "A multiphase level set framework for image segmentation using the Mumford and Shah model", UCLA CAM Report 01-25, 2001.

[BG] Claude Cohen-Bacrie, Yves Goussard, "Regularized Reconstruction in Electrical Impedance Tomography Using a Variance Uniformization Constraint" IEEE TRANSACTIONS ON MEDICAL IMAGING, VOL. 16, NO. 5, OCTOBER 1997 562-571.

It should be understood that the examples and embodiments described herein are for illustrative purposes only and that various modifications or changes in light thereof will be suggested to persons skilled in the art and are to be included within the spirit and purview of this application.

We claim:
1. A method of determining the conductivity of a sample as a function of position, comprising:
   measuring electromagnetic fields from a sample via a plurality of probes, wherein the plurality of probes detect time-varying electromagnetic fields;
   determining the measured correlation, $M_{ij}(\Omega)$, between at least one pair of probes;
   determining the conductivity of the sample as a function of position, based on the following relationship;

$$M_{ij}(\Omega) = \int_\Omega \vec{E}_i(\sigma, x) \cdot \sigma(x) \cdot \vec{E}_j(\sigma, x) \, dx$$

where $\sigma(x)$ is the complex conductivity tensor of the sample as a function of position and $E_j(\sigma, x)$ is the electric field created in the sample at position x by probe j when driven by a unit source.

2. The method according to claim 1 wherein determining the measured correlation, $M_{ij}(\Omega)$, between at least one pair of probes comprises determining the measured correlation, $M_{ij}(\Omega)$, between at least one-half of the pairs of probes.

3. The method according to claim 1, wherein measuring electromagnetic fields from a sample comprises measuring electromagnetic fields generated by the sample.

4. The method according to claim 3, wherein the electromagnetic fields generated by the sample are generated due to the resistivity of the sample.

5. The method according to claim 3, wherein the electromagnetic fields generated by the sample are dependent upon the temperature of the sample.

6. The method according to claim 1, further comprising: imaging the sample;
   wherein determining the conductivity of the sample comprises constraining $\sigma(x)$ to vary in accordance with the acquired image.

7. The method according to claim 6, wherein imaging the sample comprises imaging the sample via magnetic resonance imaging.

8. The method according to claim 7, wherein imaging the sample via magnetic resonance imaging is accomplished via a second plurality of probes.

9. The method according to claim 7, wherein imaging the sample via magnetic resonance imaging is accomplished via the plurality of probes.

10. The method according to claim 9, wherein imaging the sample via magnetic resonance imaging is accomplished at a different time from measuring electromagnetic fields from a sample.

11. The method according to claim 9, wherein imaging the sample via magnetic resonance imaging is accomplished at the same time as measuring electromagnetic fields from a sample.

12. The method according to claim 1, wherein at least one of the plurality of probes are rotated with respect to the sample during measuring electromagnetic fields from a sample,
wherein electromagnetic fields from the sample are measured over a first time period, the at least one of the plurality of probes are rotated with respect to the sample, and electromagnetic fields from the sample are measured over a second period of time.

13. The method according to claim 12, wherein the spatial relationship between each of the plurality of probes is substantially maintained as the plurality of probes are rotated with respect to the sample.

14. The method according to claim 1, wherein at least one of the plurality of probes are translated with respect to the sample during measuring electromagnetic fields from a sample,
wherein electromagnetic fields from the sample are measured over a first period of time, the at least one of plurality of probes are translated with respect to the sample, and the electromagnetic fields from the sample are measured over a second period of time.

15. The method according to claim 14, wherein the spatial relationship between each of the plurality of probes is substantially maintained as the plurality of probes are translated with respect to the sample.

16. The method according to claim 1, wherein measuring electromagnetic fields from a sample comprises measuring RF electromagnetic fields from the sample.

17. The method according to claim 1, wherein determining the measured correlation, $M_{ij}(\Omega)$, between at least one pair of probes comprises processing the analog signals from the $i^{th}$ and $j^{th}$ probes in real time in analog to determine $M_{ij}(\Omega)$.

18. The method according to claim 1, wherein determining the measured correlation, $M_{ij}(\Omega)$, between at least one pair of probes comprises converting the analog signals from the $i^{th}$ and $j^{th}$ probes into corresponding digital signals and processing the digital signals from the $i^{th}$ and $j^{th}$ probes to determine $M_{ij}(\Omega)$.

19. A method of determining the temperature of a sample as a function of position, comprising:
   measuring electromagnetic fields from a sample via a plurality of probes, wherein the plurality of probes detect time-varying electromagnetic fields;
   determining the measured correlation, $M_{ij}(\Omega)$, between at least one pair of probes;
   determining the temperature of the sample as a function of position, based on the following relationship;

$$M_{ij}(\Omega) = \int_\Omega \vec{E}_i(\sigma, x) \cdot T(x) \cdot \vec{E}_j(\sigma, x) \, dx$$

where $T(x)$ is the temperature of the sample as a function of position and $E_j(\sigma, x)$ is the electric field created in the sample at position x by probe j when driven by a unit source.

* * * * *

UNITED STATES PATENT AND TRADEMARK OFFICE
CERTIFICATE OF CORRECTION

PATENT NO.          : 6,865,494 B2
APPLICATION NO. : 10/323135
DATED                  : March 8, 2005
INVENTOR(S)         : G. Randy Duensing, Charles Saylor and Feng Huang It is certified that error appears in the above-identified patent and that said Letters Patent is hereby corrected as shown below:

On the Tile Page, Item (60)

"Provisional application No. 60/430,772, filed on Dec. 3, 2001" should read --Provisional application No. 60/430,772, filed on Dec. 3, 2002--.

Column 1,

Line 66, "stand along technique" should read --stand alone technique--.

Column 3,

Line 58, "where $E_I$, $E_k$ are the" should read --where $E_j$, $E_k$ are the--.

Column 7,

Line 56, "wherein $E_I$, $E_k$ are the" should read --where $E_j$, $E_k$ are the--.

Column 19,

Line 29, "$R_{ij}$ (x,y,)" should read --$R_{ij}$ (x,y)--.

Column 19,

Line 53, "$\sigma_k \geqq 0$ can be added" should read --$\sigma_k \geq 0$ can be added--.

Column 20,

Line 15, "number of level sets, m = log"$_2$" should read --number of level sets, m = $\log_2^n$--

Column 20,

Line 26, "class I, $1 \leqq I \leqq n$" should read --class I, $1 \leq I \leq n$--.

UNITED STATES PATENT AND TRADEMARK OFFICE
CERTIFICATE OF CORRECTION

PATENT NO. : 6,865,494 B2
APPLICATION NO. : 10/323135
DATED : March 8, 2005
INVENTOR(S) : G. Randy Duensing, Charles Saylor and Feng Huang It is certified that error appears in the above-identified patent and that said Letters Patent is hereby corrected as shown below:

Column 20,

Line 42, "class I, $1 \leqq I \leqq n$" should read --class I, $1 \leq I \leq n$--.

Column 25,

Line 1, "that a is piecewise" should read --that $\sigma$ is piecewise--.

Column 27,

Lines 66 & 67, "set phase I, $1 \leqq I \leqq n$" should read --set phase I, $1 \leq I \leq n$--.

Column 28,

Lines 3, "level set phase $1 \leqq I \leqq n$" should read --level set phase $1 \leq I \leq n$--.

Column 28,

Lines 13, "Cu2SO4" should read --$Cu_2SO_4$--.

Signed and Sealed this

First Day of January, 2008

JON W. DUDAS
*Director of the United States Patent and Trademark Office*